United States Patent [19]

Kleyer et al.

[11] Patent Number: 5,359,111
[45] Date of Patent: Oct. 25, 1994

[54] METHOD FOR CONTROLLING HYDROSILYLATION IN A REACTION MIXTURE

[75] Inventors: Don L. Kleyer, Hemlock; Binh T. Nguyen; Dale E. Hauenstein, both of Midland; Sean P. Davern, Auburn; William J. Schulz, Jr., Midland, all of Mich.

[73] Assignee: Dow Corning Corporation, Midland, Mich.

[21] Appl. No.: 99,783

[22] Filed: Jul. 30, 1993

Related U.S. Application Data

[63] Continuation of Ser. No. 991,072, Dec. 14, 1992, and a continuation-in-part of Ser. No. 9,169, Jan. 26, 1993, abandoned, which is a continuation of Ser. No. 762,672, Sep. 18, 1991, abandoned.

[51] Int. Cl.$^5$ .................................................. C07F 7/08
[52] U.S. Cl. ...................................... 556/479; 556/453; 556/456; 556/460; 556/461; 556/462
[58] Field of Search ................ 556/479, 453, 456, 460, 556/461, 462

[56] References Cited

U.S. PATENT DOCUMENTS

| | | | |
|---|---|---|---|
| 2,823,218 | 2/1958 | Speier | 260/448.2 |
| 3,220,972 | 11/1965 | Lamoreaux | 260/46.5 |
| 3,775,452 | 11/1973 | Karstedt | 260/429 R |
| 4,417,068 | 11/1983 | Kollmeier et al. | 556/479 |
| 4,578,497 | 3/1986 | Onopchenko | 556/479 |
| 4,883,569 | 11/1989 | Endo et al. | 556/479 X |

FOREIGN PATENT DOCUMENTS

| | | |
|---|---|---|
| 0337197A1 | 3/1989 | European Pat. Off. . |
| 0337197 | 10/1989 | European Pat. Off. . |
| 0460590A1 | 6/1991 | European Pat. Off. . |

OTHER PUBLICATIONS

Dickers, et al., Organosilicon Chemistry. Part 24. Homogeneous Rhodium-Catalysed Hydrosilation of Alkenes and Alkynes; The Role of Oxygen or Hydroperoxides, (1976) pp. 308-313.

Harrod, et al, Hydrosilation Catalyzed by Group VII Complexes, Org. Synth. Met. Carbonyls (1977)(2) 673-6704.

Suzuki, et al., Journal of Organometallic Chemistry, New aspects of platinum–catalyzed hydrosilylation of disilylethynes II. Effects of oxygen and temperature 396 (1990) 299-305.

Lewis, Organometallics, Hydrosilylation Catalyzed by Metal Colloids: A relative Activity Study, 1990, pp. 621-625.

Lewis, Journal of Am. Chem. Soc., on the Mechanism of Metal Colloid Catalyzed Hydrosilylation, pp. 5998-6004 (1990).

Organosilicon Chemistry. Part 24, Homogeneous Rhodium-catalyzed Hydrosilation of Alkenes and Alkynes: The role of Oxygen or Hydroperoxides By: Hugh M. Dickers et al. (1985).

On the Mechanism of Metal Colloid Catalyzed Hydrosilation: Proposed Explanations for Electronic Effects and Oxygen Cocatalysis By: Larry N. Lewis (1986).

Primary Examiner—Paul F. Shaver
Attorney, Agent, or Firm—Sharon K. Severence

[57] ABSTRACT

This invention discloses a method of controlling hydrosilylations in a reaction mixture by controlling the solution concentration of oxygen in the reaction mixture, relative to any platinum present in the reaction mixture. This invention further discloses a method for controlling isomerization in linear or branched alkenyl compounds having at least 4 carbon atoms during a hydrosilylation reaction by introducing a controlled amount of oxygen into the alkenyl compounds during the hydrosilylation. This invention further discloses a method for producing dicycloalkylsubstituted silanes by reacting a halo-or alkoxy-silane with a unsaturated cycloalkenyl compound in the presence of oxygen and a hydrosilylation catalyst.

55 Claims, 5 Drawing Sheets

METHOD FOR CONTROLLING HYDROSILYLATION IN A REACTION MIXTURE

This is a continuation of copending application(s) Ser. No. 07/991,072 filed on Dec. 14, 1992 and a continuation-in-part of copending application(s) Ser. No. 08/009,169 filed on Jan. 26, 1993, now abandoned which is a continuation of Ser. No. 07/762,672 filed on Sep. 18, 1991, now abandoned.

BACKGROUND OF THE INVENTION

One method known in the art for producing organosilicon compounds comprises reacting a silicon hydride containing compound with an unsaturated compound in the presence of a catalyst. This reaction is commonly referred to as hydrosilylation. Typically the catalyst is platinum metal on a support, a platinum compound generally used in an inert solvent, or a platinum complex, however other catalysts comprising rhodium or nickel may be used. In U.S. Pat. No. 2,823,218 to Speier, et al. a method for the production of organosilicon compounds by reacting an Si—H with a compound containing aliphatic carbon atoms linked by multiple bonds in the presence of a chloroplatinic acid is taught. U.S. Pat. No. 3,220,972 to Lamoreaux teaches a similar process however the catalyst is a reaction product of chloroplatinic acid. In EP Patent Application No. 0337197 to Lewis the catalyst used is a rhodium colloid and the silicon containing reactant must have two to three hydrogen atoms bonded to the silicon.

One of the major problems known in the art with hydrosilylations is the de-activation of the catalyst prior to the completion of the reaction. One method for reactivation of the catalyst has been to expose the reaction mixture to oxygen. For example, U.S. Pat. No. 4,578,497 to Onopchenko, et al. teaches the use of an oxygenated platinum containing catalyst for hydrosilylation with alkylsilanes, $R'R_xSiH_{3-x}$. The oxygenated platinum catalyst is produced by contacting the catalyst with an oxygen-containing gas. In particular, the catalyst is contacted with the oxygen-containing gas by bubbling air into the catalyst mixed with the olefin and with or without an inert solvent under ambient temperatures prior to the reaction. Another technique taught by Onopchenko is to run the hydrosilylation until de-activation occurs, cool to room temperature and then bubble an oxygen-containing gas into the mixture. Following the exposure to oxygen the system is placed under an inert atmosphere and the reaction is again commenced.

The method taught by Onopchenko has several disadvantages. The introduction of oxygen must always be done at room temperature. Therefore the oxygen must be introduced before starting the reaction. However, if an insufficient amount of oxygen is added then the catalyst may still de-activate, in other words, there is no control over the reaction except to stop and start the reaction. The oxygen can also be introduced once the catalyst has de-activated and the reactants have been cooled to room temperature. This results in inefficient processing and the possibility of unsafe conditions upon re-activation. Further, Onopchenko requires that the reactants be placed under an inert atmosphere after the exposure of oxygen, once again leading to the possibility of insufficient oxygen being present to sustain the reaction. Finally, Onopchenko does not provide any means for controlling the reaction rate through the use of oxygen, as in his disclosure, the reaction goes or it does not go.

Dickers, et al., "Organosilicon Chemistry. Part 24 Homogeneous Rhodium-Catalysed Hydrosilylation of Alkenes and Alkynes: The Role of Oxygen or Hydroperoxides", J. Chem. Soc., Dalton Trans. (1980) (2) 308; disclose the use of oxygen to initiate the hydrosilylation of propene, hex-1-ene and hex-1-yne using [RhCl(PPh$_3$)$_3$] as the catalyst. The oxygen is necessary when the reagents have been purified.

Finally, in Harrod, J. F. and Chalk, A. J. "Hydrosilation Catalyzed by Group VIII Complex", Org. Synth. Met. Carbonyls. (1977) (2) 673–704, at pages 682 and 683, there is disclosed the fact that oxygen is a co-catalyst in hydrosilylations and that this is known among people who run hydrosilylations on a large scale where deliberate aeration of the reaction may be required to sustain catalytic activity. Chalk and Harrod merely reiterate that oxygen has an impact on hydrosilylation and on page 683, they speculate as to how it does impact hydrosilylation, but they never do disclose the key to controlling hydrosilylation.

Thus it is an object of this invention to provide a process for controlling hydrosilylation in a reaction mixture by controlling the solution concentration of oxygen relative to any platinum in said reaction mixture.

It is further an object of this invention to provide a process for controlling isomerization in linear or branched alkenyl compounds having at least 4 carbon atoms by introducing oxygen into the reaction mixture during the hydrosilylation reaction.

It is further an object of this invention to provide a means for producing dicycloalkylsubstituted silanes by reacting a silane selected from the group consisting of halo- or alkoxy- silanes having two hydrogen atoms bonded to the silicon or monocycloalkylsubstituted halo- or alkoxy- silanes having one hydrogen atom bonded to the silicon with an unsaturated cycloalkenyl compound or mixture of cycloalkenyl compounds having at least 4 carbon atoms in the presence of a hydrosilylation catalyst and oxygen.

SUMMARY OF THE INVENTION

The instant invention deals with a method of controlling hydrosilylation involving reacting silicon hydrides having 1 to 3 hydrogen atoms attached to the silicon with unsaturated compounds to produce organosilicon compounds. The reaction is catalyzed using a platinum catalyst selected from platinum metal, platinum compounds and platinum complexes. Oxygen is introduced during the reaction to control the reaction rate, and isomerization in branched or linear alkenyl compounds, among other things.

This invention further deals with a method of producing dicycloalkylsubstituted silanes by reacting a silane selected from the group consisting of halo- or alkoxy-silanes having two hydrogen atoms bonded to the silicon or monocycloalkylsubstituted halo- or alkoxy-silanes having one hydrogen atom bonded to the silicon with an unsaturated cycloalkenyl compound or mixture of cycloalkenyl compounds having at least 4 carbon atoms. The reaction is catalyzed with a hydrosilylation catalyst selected from rhodium compounds, platinum metal, platinum compounds, platinum complexes, nickel compounds, and others. Oxygen is introduced throughout the reaction to enhance reaction parameters such as reaction rate and selectivity of addition.

THE INVENTION

This invention is directed to a method of controlling hydrosilylation in a reaction mixture by controlling the solution concentration of oxygen relative to any platinum in said reaction mixture said hydrosilylation comprising (A) a silicon hydride selected from silicon hydrides having the general formulae:

(i) $R_xSiH_{4-x}$
(ii) $R_yH_uSiX_{4-y-u}$
(iii) $R_z(R'O)_{4-z-w}SiH_w$

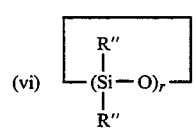

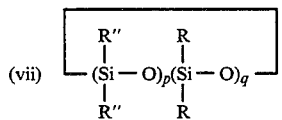

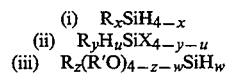

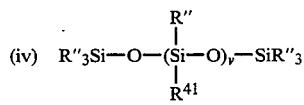

and

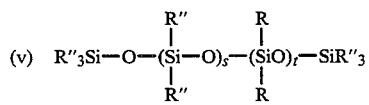

wherein each R is independently selected from the group consisting of substituted and unsubstituted alkyl groups having 1 to 30 carbon atoms, substituted and unsubstituted cycloalkyl groups having at least 4 carbon atoms and substituted and unsubstituted aryl groups having 6 to 16 carbon atoms; each R' is independently selected from alkyl groups having 1 to 6 carbon atoms; R" is independently selected from the group consisting of R and the hydrogen atom, with the proviso that at least one R" in each molecule is a hydrogen atom; X is a halide; p has a value of at least one; q has a value of at least 1 with the proviso that p+q has a value of 3 to 8; r has a value of 3 to 8; s has a value of 1 or greater; t has a value of 1 or greater; u has a value of 1, 2, or 3 with the proviso that u+y≦3; v has a value of zero or an integer of 1 or greater; w has a value of 1 to 3; x has the value of 1 to 3; y has a value of 0 to 2; and z has a value of 0 to 2 with the proviso that w+z≦3, with (B) unsaturated compounds selected from the group consisting of
  (i) substituted or unsubstituted unsaturated organic compounds or mixtures thereof,
  (ii) substituted or unsaturated unsaturated silicon compounds or mixtures thereof and,
  (iii) mixtures of (i) and (ii);
in the presence of a hydrosilylation catalyst selected from the group consisting of (a) platinum metal on a support, (b) platinum compounds, (c) platinum complexes, (d) rhodium compounds, (e) nickel compounds and others.

The presence of the oxygen during the reaction enhances reaction parameters such as reaction rate and selectivity of addition when the solution concentration of oxygen is controlled relative to any platinum in the reaction mixture. In addition the presence of the oxygen during the reaction controls isomerization in branched or linear alkenyl compounds employed in the hydrosilylation reaction.

As noted above, the silicon hydrides useful in the instant invention may be exemplified by compounds or mixtures of compounds of the formulae:

(i) $R_xSiH_{4-x}$
(ii) $R_yH_uSiX_{4-y-u}$
(iii) $R_z(R'O)_{4-z-w}SiH_w$

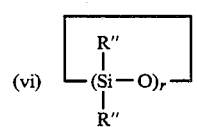

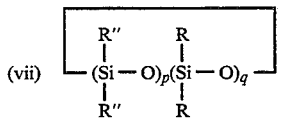

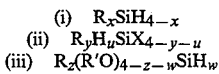

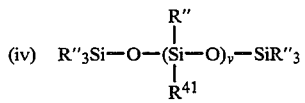

and

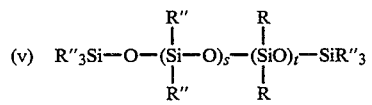

The silicon hydrides useful in the instant invention may be specifically exemplified by, but not limited to, trimethylsilane, dimethylphenylsilane, dimethylsilane, dichlorosilane, dimethoxysilane, methyldimethoxysilane, triethylsilane, triethoxysilane, trichlorosilane, methyldichlorosilane, dimethylchlorosilane, trimethoxysilane, 1,1,1,2,3,3,3-heptamethyltrisiloxane, cyclopentyldichlorosilane, cyclohexyldichlorosilane, dimethylsiloxane/methylhydrogensiloxane copolymers, methylhydrogencyclic siloxanes, and others.

The silicon hydride is reacted with unsaturated compounds selected from the group consisting of (i) substituted or unsubstituted unsaturated organic compounds or mixtures thereof, (ii) substituted or unsubstituted unsaturated silicon compounds or mixtures thereof and, (iii) mixtures of (i) and (ii). More specific examples of the unsaturated compounds being unsubstituted cycloalkenyl compounds having at least 4 carbon atoms, substituted cycloalkenyl compounds having at least 4 carbon atoms, linear alkenyl compounds having 2 to 30 carbon atoms, branched alkenyl compounds having 4 to 30 carbon atoms, and mixtures thereof, and the like.

The substituted and unsubstituted cycloalkenyl compounds useful in the instant invention are those olefins that contain one or more unsaturated carbon-carbon bond in the ring. The unsubstituted cycloalkenyl compounds may be further exemplified by, but not limited to, cyclobutene, cyclopentene, cyclohexene, cycloheptene, cyclooctene, cyclopentadiene, 1,3-cyclohexadiene, 1,3,5,7-cycloheptadiene, and cyclooctatetraene.

The substituted cycloalkenyl compounds useful in the instant invention are only those that contain substitution on the saturated carbon (i.e. not at the C═C bond). The substituted unsaturated alicyclic compounds useful in the instant invention may be further exemplified by, but no limited to 3-methylcyclopentene, 3-chlorocyclobutene, 4-phenyl-cyclohexene and 3-methylcyclopentadiene. The preferred cycloalkenyl compounds are cyclohexene and cyclopentene.

The unsaturated cycloalkenyl compounds useful in the instant invention are commercially available. Prior to the reaction of the unsaturated cycloalkenyl compound it may be preferable to treat or purify the unsaturated cycloalkenyl compound. Methods which can be used for treating or purifying the unsaturated cycloalkenyl compound are those methods known in the art and include but are not limited to distillation, treatment with alumina and others.

Other compounds that are useful in this invention are unsaturated linear and branched alkyl compounds which include, but are not limited to those compounds with terminal unsaturation such as 1-hexene, and those compounds with internal unsaturation such as trans-2-hexene.

Other compounds such as olefinically unsaturated functional alkenyl compounds which contain halogen, oxygen in the form of acids, anhydrides, alcohols, esters, and ethers, and nitrogen, may be used in the instant invention.

The halogenated olefinically unsaturated functional alkenyl compounds which may be used herein may be exemplified by compounds such as vinyl chloride, allyl bromide, allyl iodide, allylene bromide, tri- and tetra-chloroethylene, tetrafluoroethylene, chloroprene, vinylidene chloride, and dichlorostyrene.

Suitable oxygen containing olefinically unsaturated functional alkenyl compounds may be exemplified by ethers such as the allyl and vinyl ethers, alcohols such as allyl alcohol (vinyl carbinol), methylvinylcarbinol and ethynyldimethylcarbinol, acids such as acrylic, methacrylic, vinylacetic, oleic, sorbic, linolenic, and chaulmoogric, and esters such as vinyl acetate, allyl acetate, butenyl acetate, allyl stearate, methylacrylate, ethylcrotonate, diallyl succinate and diallyl phthalate. Suitable nitrogen containing olefinically unsaturated functional alkenyl compounds may be exemplified by indigo, indole, acrylonitrile, and allyl cyanide.

Specifically included within the definition of olefinic unsaturated groups are those olefinic unsaturated groups that are substituted by organofunctional moieties such as $$CH_2\!=\!CHCH_2OC(O)C(CH_3)\!=\!CH_2,$$

$$CH_2\!=\!CHCH_2NHCH_2CH_2NH_2,$$

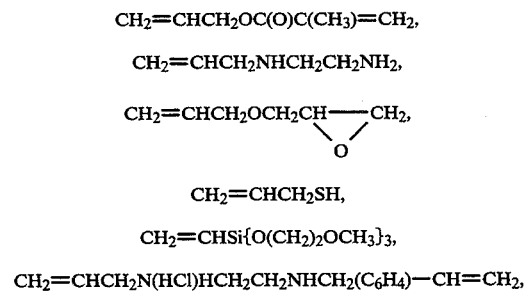

$$CH_2\!=\!CHCH_2SH,$$

$$CH_2\!=\!CHSi\{O(CH_2)_2OCH_3\}_3,$$

$$CH_2\!=\!CHCH_2N(HCl)HCH_2CH_2NHCH_2(C_6H_4)\!-\!CH\!=\!CH_2,$$

and the like.

Unsaturated silicon compounds that are useful in this invention are for example $(CH_2\!=\!CH)_aSi(OR')_{3-a}$ wherein R' has the same meaning as that set forth above and a has a value of 1 or 2, $CH_2\!=\!CHCH_2Si(OR')_3$ and $CH_2\!=\!CHCH_2Si(CH_3)(OR')_2$, and the like.

The unsaturated compounds useful in the instant invention are commercially available. Prior to the reaction of the unsaturated compound it may be preferable to treat or purify the unsaturated compound. Methods which can be used for treating or purifying the unsaturated compound are those methods known in the art and include but are not limited to distillation, treatment with alumina and others.

The relative amounts of silicon hydride and unsaturated compound employed in the process herein have no technical limitations. One unsaturated linkage, for example, ethylene, is obviously the stoichiometric requirement per silicon bonded hydrogen atom. However there is no absolute necessity for equivalent amounts of the reactants to be employed and any desired excess of either reactant can be present. In fact an excess of one reactant, typically the unsaturated compound, may often be desirable to force the reaction to completion or to make the greatest use of the reactant which is the most expensive or most rare. Thus the choice of reactant ratios is mostly a matter of practicality and economics based upon the reactants employed. It is preferred to use a reactant ratio ranging from 1:20 to 20:1 in terms of equivalents of Si—H compound to unsaturated compound, the more usual operating range being in the region of from 1:2 to 2:1.

In some cases it may be desirable to employ also a solvent for one or both of the reactants. The amount of solvent employed is not critical and can vary without limit except for economic considerations. Any solvent can be employed which will dissolve but be inert toward the desired reactants under the conditions of the reaction and which will not interfere with the reaction. The solvent should also be selected so that easy separation of the products after the reaction can be enhanced.

The reaction between the silicon hydride and unsaturated compound is catalyzed using a hydrosilylation catalyst. Hydrosilylation catalysts useful in the instant invention may be exemplified by, but not limited to rhodium compounds, platinum metal, platinum compounds, platinum complexes, nickel compounds and others.

Any hydrosilylation catalyst which affects the reaction between the silicon hydride at an —Si—H and the unsaturated compound at the —C═C— may be useful in the instant invention. The preferred hydrosilylation catalyst is chloroplatinic acid.

The rhodium compounds useful in the instant invention may be exemplified by rhodium chloride and $RhCl_3(n\text{-}Bu_2S)_3$.

The platinum catalysts useful in the instant invention may be selected from platinum metal on a support, platinum compounds and platinum complexes. The platinum compounds and platinum complexes may be exemplified by chloroplatinic acid, chloroplatinic acid hexahydrate, Karstedt's catalyst (Pt #2, Pt(ViMe₂Si-OSiViMe₂)₂), dichloro-bis(triphenylphosphine)-platinum(II), cis-dichloro-bis(acetonitrile)platinum(II), dicarbonyldichloroplatinum(II), platinum chloride, platinum oxide and others. The platinum metal can be deposited on a support such as charcoal, alumina, zirconia, among others. Any platinum containing material which effects the reaction between the silicon hydride and the unsaturated portion of the unsaturated compound is useful in the instant invention.

Suitable amounts of the platinum containing compounds and the platinum complexes vary within wide limits. Concentrations on the order of 1 mole of catalyst (providing one mole of platinum) per billion moles of unsaturated groups in the unsaturated compound may be useful. Concentrations as high as 1 to 10 moles of catalyst per thousand moles of unsaturated groups in the unsaturated compound may also be employed. Generally the economics of the reaction dictates the particular level of catalyst employed. Preferable concentrations are from 1 mole of platinum per 1,000 moles of unsaturated groups to 1 mole of platinum per 1,000,000 mole of unsaturated groups in the unsaturated compound. Suitable amounts of supported platinum include, for example, from about 0.1 to about 10 weight percent, preferably from about 0.5 to 5 weight percent based upon elemental platinum.

A further description of platinum catalysts useful in the instant invention is found in, but not limited to, U.S. Pat. Nos. 4,578,497, 3,775,452, 3,220,972 and 2,823,218, herein incorporated by reference for what they teach about platinum catalysts per se.

The catalyst may be dissolved in a solvent for ease of handling and to facilitate measuring the minute amounts needed. Preferably the solvent should be inert. Suitable solvents include the various hydrocarbon solvents such as benzene, toluene, xylene, and mineral spirits and polar solvents such as alcohols, various glycols and esters.

The reaction temperature can vary over an extremely wide range. The optimum temperature depends upon the concentration of catalyst present, concentration of oxygen and the nature of the reactants. Best results are obtained by initiating the reaction at about 20° to 250° C. and maintaining the reaction within reasonable limits of this range. The reaction is typically exothermic and the reaction temperature can be maintained by controlling the rate of addition of one of the reactants or applying cooling means to the reaction vessel. It is preferred to use an operating temperature such that the reaction is carried out under reflux conditions.

The reaction can be carried out at atmospheric, subatmospheric, or superatmospheric pressures. The choice of conditions is largely a matter of choice based on the nature of the reactants and the equipment available. Non-volatile reactants are especially adaptable to being heated at atmospheric pressure. It may be preferred under certain conditions to run the reaction at pressures above atmospheric to reduce the volatility of the reactants at higher temperatures.

The amount of time for the reaction to go to completion depends upon the reactants, reaction temperature, catalyst concentration, and oxygen concentration. Determination of when the reaction has gone to completion can be accomplished by simple analytical methods such as gas liquid chromatography or by infrared spectometry.

The reaction may be run on a continuous, semi-continuous, or batch reactor. A continuous reactor comprises a means wherein the reactants are introduced and products are withdrawn simultaneously. The continuous reactor may be a tank, a tubular structure, a tower, or some other like structure, the overall design not being essential. A semi-continuous reactor comprises a means wherein some of the reactants are charged at the beginning and the remaining are fed continuously as the reaction progresses. The product may optionally be simultaneously be withdrawn from the semi-continuous reactor. A batch reactor comprises a means wherein all the reactants are added at the beginning and processing is carried out according to a predetermined course of reaction during which no reactant is fed into or removed from the reactor. Typically a batch reactor will be a tank with or without agitation means.

In the instant invention, the reaction is carried out in the continuous presence of oxygen. The oxygen, when added in controlled amounts during the course of the reaction, provides a means for controlling the rate of the reaction, enhancing the selectivity of addition and for controlling isomerization in linear or branched alkenyl compounds having at least 4 carbon atoms.

The oxygen is added into the reaction mixture by bubbling it into either one of the reactants or by bubbling it into the reaction mixture or providing the oxygen in the head space of the reactor. Subsurface addition of oxygen into the reaction mixture on a continuous basis is most preferred since it allows for quicker equilibration of its solution concentration. In other words, it is the solution concentration of the oxygen relative to the platinum that is important. Contacting the oxygen on the surface of the liquid, such as by blowing it into the vapor space of the reactor or by purging the reactor system with oxygen, will not be as efficient, but in some cases may be the safest manner of providing the needed oxygen.

The amount of oxygen which must be added will be dependent on the operating conditions, the reactants and the amount of catalyst present. It is preferred to introduce the oxygen combined with an inert gas at an oxygen level of from 1 part per million to 90 weight percent, more preferably 1 to 5 weight percent. The inert gas which the oxygen is combined with may be selected from any inert gas such as nitrogen, argon and others.

The amount of oxygen is important to the rate of the reaction. If too much oxygen is added then the reaction may proceed slowly or not at all. Also, the presence of too much oxygen may result in the formation of undesirable by-products and oxidation products. Further, the presence of too much oxygen may create unsafe operating conditions because of explosive conditions that result with certain silicon hydrides in the presence of too much oxygen. If too little oxygen is added then again the rate of the reaction will be slow, the reaction may not proceed at all or the catalyst may deactivate before the reaction has gone to completion. One skilled in the art will be able to determine the optimum amount of oxygen necessary to provide the desired operating conditions and product distribution.

The instant invention is particularly useful for the production of dicycloalkylsubstituted silanes. The dicycloalkylsubstituted silanes of the instant invention may be produced by several reaction routes. One reaction route comprises producing a monocycloalkylsubstituted halo- or alkoxy-silane having a hydrogen attached to the silicon (monohydridosilane), represented by the formulas

X$_2$R'''SiH and

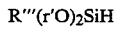

R'''(r'O)$_2$SiH wherein R' independently selected from alkyl groups having 1 to 6 carbon atoms, X is a halide and R''' is a cycloalkyl having at least 4 carbon atoms. R''' may be further exemplified by, but not limited to, cyclobutyl, cyclopentyl, cyclohexyl and others. The preferred R''' is cyclopentyl.

The monohydridosilane may be produced by any method known in the art. The preferable method for forming the monohydridosilane is to react an unsaturated cycloalkenyl compound (substituted or unsubstituted) with a silane having two hydrogen atoms attached to the silicon (herein referred to as silane). It is preferable to carry out this reaction under an inert atmosphere. However, oxygen may be introduced to facilitate the formation of the monohydridosilane. There is no limitation to the ratio of the silane and unsaturated cycloalkenyl compounds in the reaction to produce the monoydridosilane. It is preferred to use at least one mole of unsaturated cycloalkenyl compound (providing one mole of C=C) for every mole of silane (providing two moles of Si—H). It is more preferable to use between 8 to 12 moles of unsaturated cycloalkyenyl compound for every mole of silane.

The resulting monohydridosilane is reacted with an unsaturated cycloalkyenyl compound (substituted or unsubstituted) using a hydrosilylation catalyst in the presence of oxygen to produce the dicycloalkylsubstituted silane. Again there is no limitation to the ratio of monohydridosilane and unsaturated cycloalkyenyl compound in the reaction however, it is preferable to use greater than one mole of unsaturated cycloalkyenyl compound for every mole of monohydridosilane and even more preferable to use between 1.1 to 20 moles of unsaturated cycloalkyenyl compound for every mole of monohydridosilane.

Another method by which the dicycloalkylsubstituted silane may be produced comprises directly reacting an unsaturated cycloalkyenyl compound with a halo- or alkoxy-silane having two hydrogen atoms attached to the silicon (dihydridosilane) represented by the formulas

$H_2SiX_2$ and

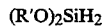

$(R'O)_2SiH_2$ wherein each R' is independently selected from alkyl groups having 1 to 6 carbon atoms, and X is a halide; using a hydrosilylation catalyst in the presence of oxygen. There is no limitation to the ratio of dihydridosilane and unsaturated cycloalkyenyl compound in the reaction. It is preferred to use at least two moles of unsaturated cycloalkyenyl compound (providing two moles of C=C) for every mole of dihydridosilane (providing two moles of —SiH). It is more preferable to use between 2.1 to 20 moles of unsaturated cycloalkyenyl compound for every mole of dihydridosilane.

Either reaction route by which the dicycloalkylsubstituted silane is produced requires the presence of an effective amount of oxygen. In the first route the presence of oxygen is required when adding the cycloalkyenyl compound to the monohydridosilane. The second reaction route requires the continuous presence of oxygen. The oxygen provides a means for controlling the rate of the reaction, enhancing the addition of the alicyclic group to the monohydrido- or dihydrido-silane and possibly controlling the by-product formation resulting in a higher yield of the dicycloalkylsubstituted silane. The oxygen is added into the reaction mixture by bubbling it into one of the reactants or by bubbling it into the reaction mixture. The addition of oxygen into the reactants on a subsurface basis is most preferred since it allows for enhanced mass transfer leading to quicker equilibration of its solution concentration. In other words, it is the solution concentration of the oxygen relative to the platinum which is important. Contacting the oxygen on the surface of the liquid, such as by blowing it into the vapor space of the reactor or by purging the reactor system with oxygen, may not be as effective.

The effective amount of oxygen which must be added will be dependent on the operating conditions, the reactants and the amount of catalyst present and can be readily determined by one skilled in the art. It is preferred to introduce the oxygen into the reaction system combined with an inert gas at an oxygen level of parts per million to 99+weight percent, more preferably 0.1 to 40 weight percent. The inert gas which the oxygen is combined with may be selected from any inert gas such as nitrogen, argon and other.

The amount of oxygen added during the reaction will affect the rate of reaction and by-product formation. If too little oxygen is added then addition to form the dicycloalkylsubstituted silane may proceed slowly or not at all. For example the reaction between the monohydridosilane and the unsaturated cycloalkyenyl compound may not take place or may proceed slowly or the reaction between the unsaturated cycloalkyenyl compound and dihydridosilane may proceed to form the monohydridosilane and little or none of the dicycloalkylsubstituted silane. The presence of too much oxygen may result in the formation of undesirable by-products such as oxidation products. Further, the presence of too much oxygen may create unsafe operating conditions because of explosive conditions that result with the dihydridosilanes in presence of too much oxygen. One skilled in the art will be able to determine the optimum amount of oxygen necessary to provide the desired operating conditions and product distribution. Typically one skilled in the art will be able to make such a determination by monitoring the rate of the reaction and the by-product formation.

Figure 1:
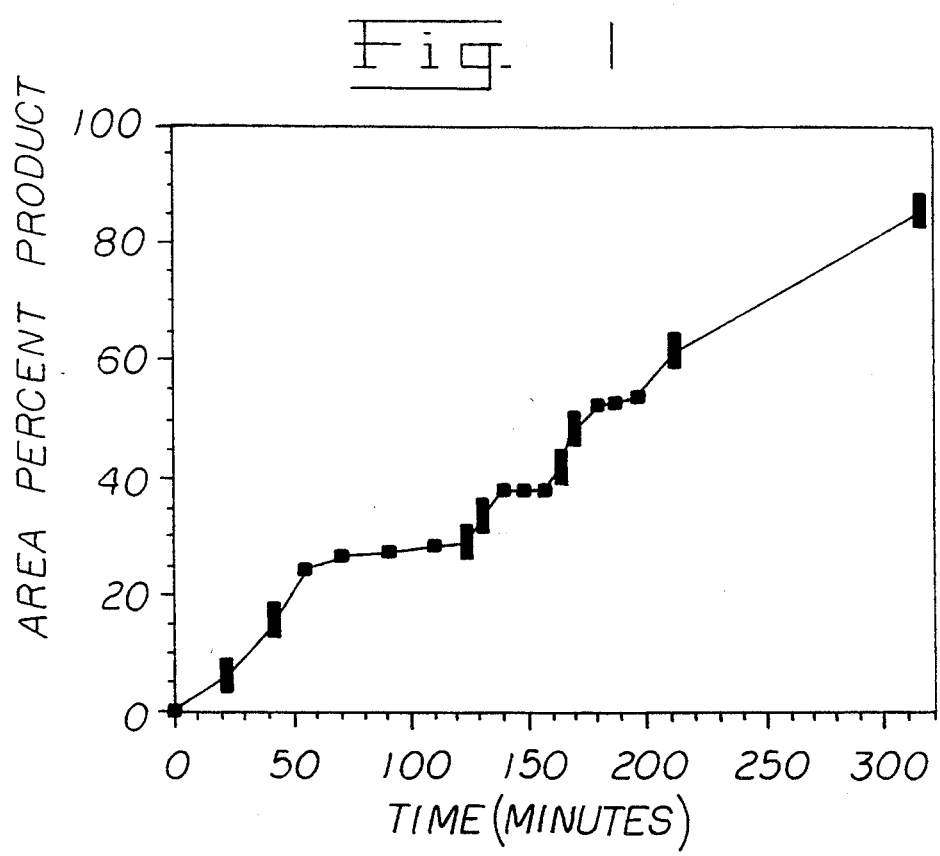
FIG. 1 plots the hydrosilylation rate with and without $O_2$.

So that those skilled in the art can understand and appreciate the invention taught herein, the following examples are presented, it being understood that these examples should not be used to limit the scope of this invention found in the claims attached hereto.

EXPERIMENTAL PROCEDURE

EXAMPLES 1-8

Examples 1-8 were carried out in a 250 ml, three-necked round bottomed flask equipped with a thermometer, a thermowatch set at 53° C., a reflux condenser surmounted with a dry ice condenser connected to a bubbler, a thermometer adaptor fitted with a 23 cm. long disposable pipet for subsurface addition of the reagent gas, a heating mantle and a stirbar. The reagent gas (flowrate range of 5 to 30 mL/Min.) was passed through a 10" long tube packed with dry Drierite (CaSO$_4$) drying agent before being added. The experiments used 150±1 gram of a 1:1 molar premix of cyclohexene and methyldichlorosilane wherein 150 grams of premix contained 87.5 grams of methyldichlorosilane and 62.5 grams of cyclohexene (0.76 moles each). The reaction was catalyzed using either 191 microliters of 10% by weight solution of chloroplatinic acid in isopropanol or 134 microliters of platinum #2 (a platinum complex with 1,2-divinyl-1,1,2,2,-tetramethyldisiloxane, 4.22 weight % platinum) unless otherwise noted.

The reactants were combined in the 250 mL flask and sparged with a minimum of 15 minutes of the reagent gas. The reactants were heated rapidly to 53° C., gentle reflux. The starting time of the experiment was when the solution reached 53° C. Subsurface addition of the reagent gas continued throughout the reaction.

Reflux conditions were used for most of the examples because of the resulting ease it afforded in controlling the solution concentration of oxygen. It was found when monitoring the solution concentration of oxygen during the portion of Example 3 which used air as the oxygen source, that at maximum rate the solution concentration of oxygen was below that achieved by subsurface addition of nitrogen when at room temperature. Thus in most of the examples, reflux was used to assist in deoxygenation of the reaction mixtures and an oxygen containing gas was then added to restore the level of oxygen needed for oxygen enhancement.

Reaction progress was monitored by removing the gas inlet thermometer adaptor and sampling with a disposable pipet into a Gas Chromatograph (GC) autosampler vial. Gas chromatographic analysis, within a minute of sampling, provided a GC area percent of product which was used directly for all discussions in this specification.

The gas chromatographic analysis was conducted on a Hewlett Packard 5710 gas chromatograph equipped with a 20'×⅛" 10% SE30 on Chromosorb W HP 80/100 mesh column purchased from Supelco Co. The gas chromatograph was operated isothermally at 160° C. and a thermal conductivity detector was used. A Hewlett Packard 3380 recording integrator was used for quantification.

Example 1

Purging a mixture of cyclohexene, methyldichlorosilane and 100 ppm chloroplatinic acid with argon then heating to 53° C., gentle reflux conditions at atmospheric pressure for 1023 minutes gave only 2% conversion to the product, cyclohexylmethyldichlorosilane. Introduction of air after 1023 minutes gave complete conversion to product in 120 minutes. Thus it was found that a component of air was necessary to enhance the desired reaction.

Example 2

The experiment in Example 1 was repeated, alternating between the subsurface addition of air and argon. It is evident that the hydrosilylation rate can be switched on and off by the choice of atmosphere as shown in FIG. 1 wherein - - - ■ - - - ■ - - - ■ - - - is the period during which argon was added to the reaction mixture, and - - - ■ - - - ■ - - - ■ - - - is the period that air was added to the reaction mixture. The three flat regions indicated by - - - ■ - - - ■ - - - ■ - - - correspond exactly with the switch to argon. The effect can also be followed visually with the solution being a dark golden color during the active period and clear, light yellow during the active time. Thus, oxygen was involved in the catalytic cycle yet no products incorporating oxygen were observed. A similar experiment conducted with platinum #2 concentrate as the catalyst source led to similar results. Also, the irreversible formation of a platinum colloid was not responsible for the yellow color associated with a hydrosilylation, since switching between clear and golden (yellow) was done simply by choice of atmosphere. It is theorized that the catalyst is responsible for the golden color.

Example 3

Figure 2:
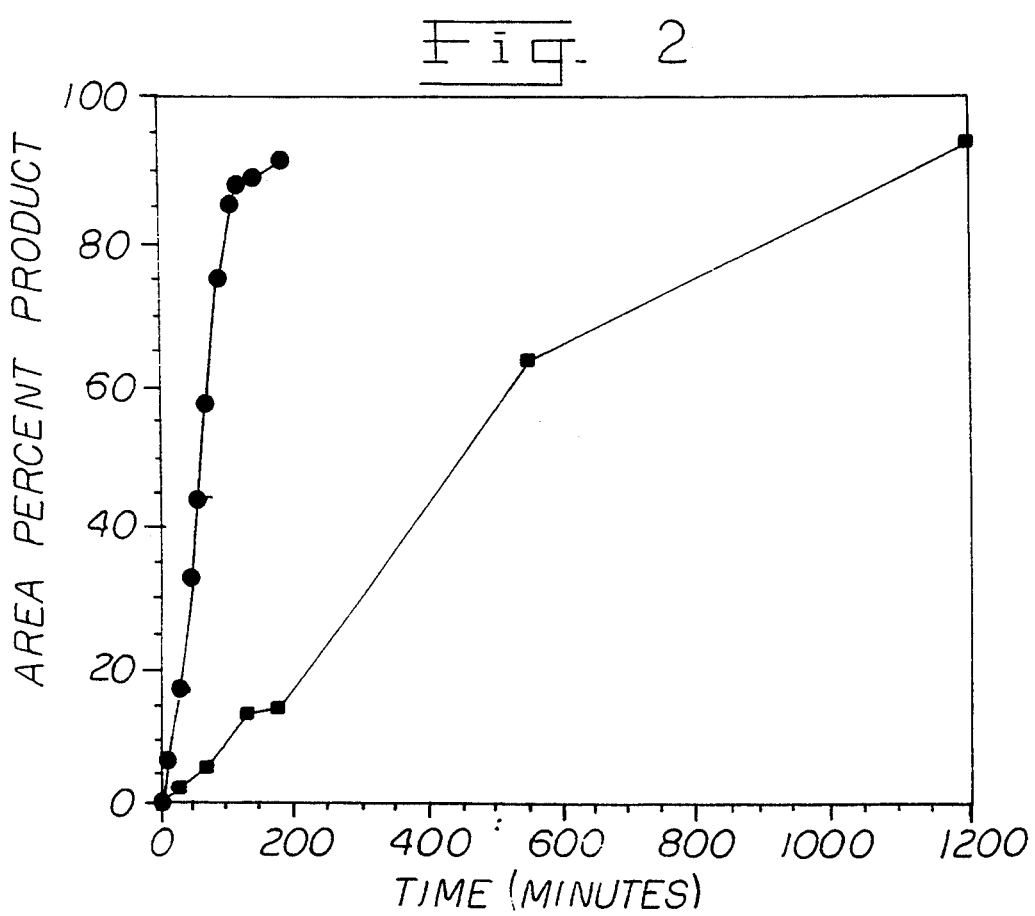
FIG. 2 plots optimum $O_2$ concentration for maximum rate.

In this example the effect of solution concentration of oxygen was examined. The hydrosilylation rate was determined with the subsurface addition of 2% O$_2$ in N$_2$. For comparison purposes a plot of the area percent of product versus time is shown in FIG. 2, for experiments which used either air or 2% O$_2$ in N$_2$ wherein - - - ● - - - ● - - - is common plant air and - - - ■ - - - ■ - - - ■ - - - is 2% O$_2$/98% N$_2$. There was a vast difference in rate showing that there is an optimum oxygen solution concentration necessary for maximum rate.

Example 4

Since subsurface addition of air greatly enhanced the rate of hydrosilylation, the experiment in Example 3 was repeated with pure dried oxygen. After 60 minutes, only 6% starting material had been converted to product. The solution remained colorless. Switching from the subsurface addition of oxygen to the subsurface addition of air allowed the reaction to proceed to completion but at a reduced rate. Repeating the experiment with 270 minutes of subsurface addition of pure dried oxygen gave an even slower hydrosilylation rate once air was introduced, 40% conversion after 24 hours. Several unexpected products were formed. The most notable were 10 area % methyltrichlorosilane along with smaller amounts of cyclohexyl chloride, several low molecular weight siloxanes and polysilanes.

Example 5

In this example the catalyst level was decreased to look at the effect of the ratio of oxygen to platinum in solution. At 50 ppm chloroplatinic acid, one half the concentration of other experiments and using subsurface addition of air as an oxygen enhancer, the rate was slower. After 5 hours at 53° C. only 43% conversion had taken place and the solution was starting to turn colorless from the earlier observed golden color. Upon further heating, products formed, as observed when pure oxygen was used with 100 ppm chlorplatinic acid (see example 4). The hydrosilylation rate also decreased. After 1400 minutes, only 66% conversion was observed. Thus the solution concentration ratio of platinum to oxygen is critical for maximum hydrosilylation rate.

Example 6

This experiment was performed to see if oxygen was necessary for hydrosilylation of a 1-alkene. When a 1:1 molar ratio solution of methyldichlorosilane and 1-hexene with 100 ppm chloroplatinic acid was degassed at 0° C. by purging with argon and then allowed to warm, hydrosilylation proceeded with sufficient vigor that the volatile contents removed themselves from the apparatus. This finding was not totally unexpected since even with extended argon purging of a methyldichlorosilane and cyclohexene solution, using chloroplatinic acid as the catalyst, 2% conversion was observed upon heating to reflux. After reflux further deoxygenated the solution, no more hydrosilylation took place even after an extended period of reflux time. With 1-hexene, which was expected to undergo hydrosilylation at a faster rate than cyclohexene, however, the initial hydrosilylation rate was vigorous.

Example 7

Figure 3:
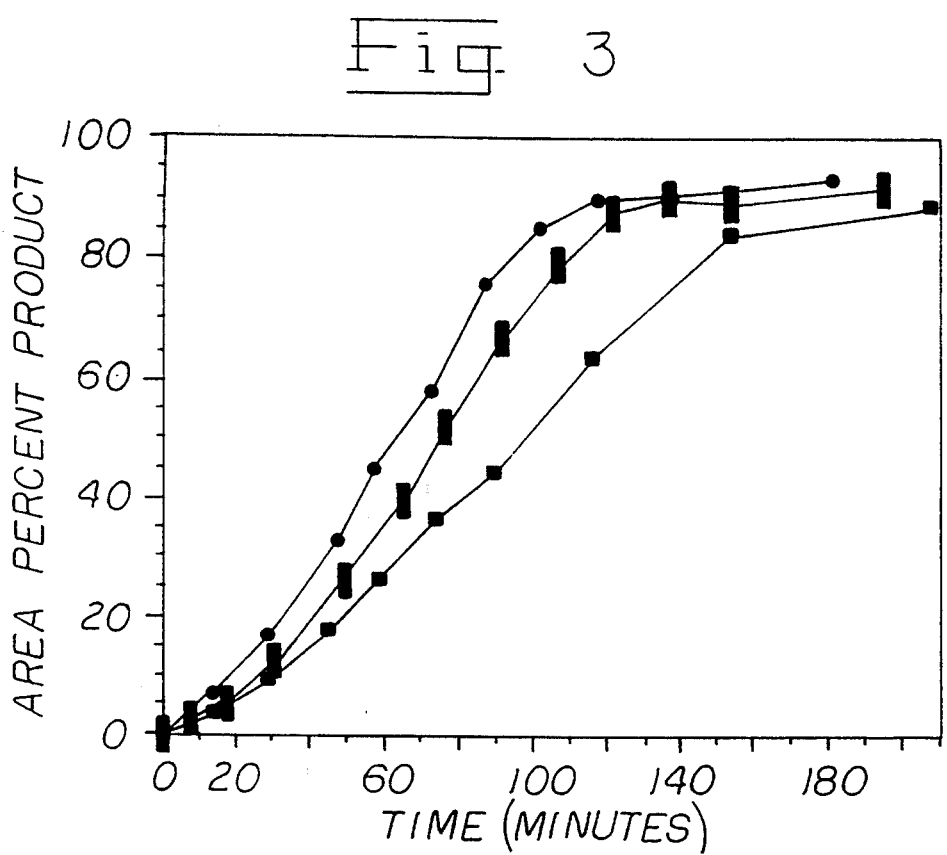
FIG. 3 compares rate of reaction when adding air subsurface to that when adding zero air subsurface.

This experiment compared the rate of reaction when adding air subsurface to that when adding zero air subsurface. The purpose was to show unequivocally which of the many components of air was effecting the hydrosilylation. Zero air is a blend of pure oxygen and pure nitrogen at the same proportions as air. As shown in FIG. 3 wherein - - - ● - - - ● - - - ● - - -is plant air, - - - ■ - - - ■ - - - ■ - - - is plant air repeated, and - - - ■ - - - ■ - - - ■ - - -is pure air, there were slight differences in rate but the differences were insignificant once one takes into account the inconsistent way in which the reagent gas was introduced into the solutions (flow rate range 5 to 30 mL/min). Since it was shown that hydrosilylation does not proceed at a significant rate when an inert gas such as argon or nitrogen was used, the fact that zero air accelerates the rate proves that oxygen is responsible for the rate enhancement.

Example 8

Figure 4:
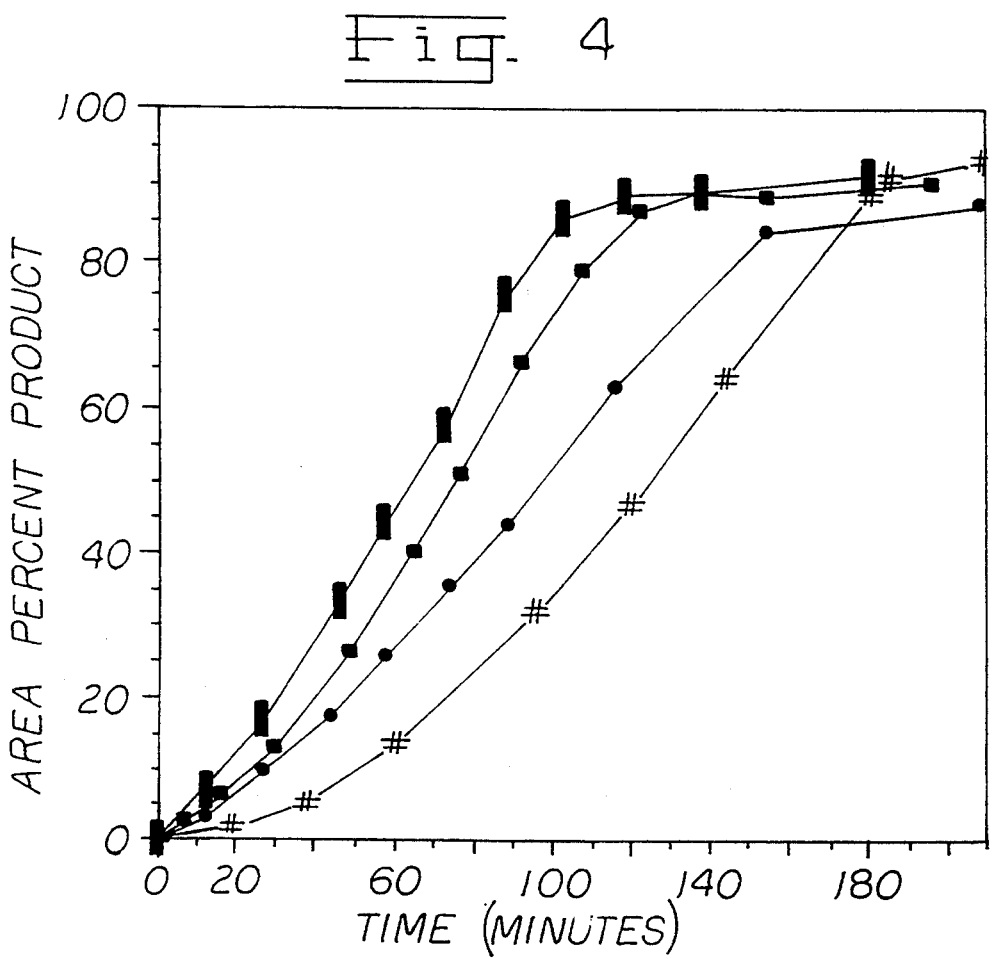
FIG. 4 plots the effect of air and light year reaction rates.

The effect of light upon the rate of hydrosilylation was investigated. A European patent application 0278863 to Takamizawa, et al. suggests that greatly enhanced rates will be achieved. When the experimental apparatus, constructed of pyrex glass, was irradiated with a 275 watt Norelco sunlamp placed 2.5 inches from the pyrex, no enhancement of rate was observed during the subsurface addition of air which is shown in FIG. 4 wherein is added air, - - - ■ - - - ■ - - - ■ - - - is added air, - - - ■ - - - ■ - - - ■ - - - is air added in repeat, - - - ● - - - ● - - - ● - - - is air added repeat and - - - # - - - # - - - # - - -is air and light. The observed slower rate during photolysis can be explained by the light heating the apparatus and lowering oxygen solubility. Irradiation of an argon degassed mixture of cyclohexene, methyldichlorosilane and chloroplatinic acid held at 53° C. gave 1.5% product after 994 minutes. This is comparable to the 2% conversion observed after 1023 minutes during thermal conditions as set forth in Example 1. Turning off the light and introducing air subsurface gave >90% conversion in 100 minutes. Thus, light does not enhance the rate of hydrosilylation.

EXPERIMENTAL PROCEDURE

EXAMPLE 9-14

Examples 9-11 and 15-17 were carried out in a 100 mL four-necked round bottomed flask equipped with a thermometer, a thermowatch set at a point to maintain gentle reflux of the starting materials, reflux condenser surmounted by a dry ice condenser connected to a bubbler gas exit, thermometer adaptor fitted with a 15 cm long disposable pipet for the subsurface addition of a gas (at 9 mL/min. unless otherwise noted), a heating mantle and a magnetic stirring bar at 1" in length. The reagent gas was passed through a 8" long tube packed with dry Drierite ($CaSO_4$) drying agent before being introduced into the reactants.

A 10% by weight solution of chloroplatinic acid ($H_2PtCl_6.6H_2O$, FW 517.93) in isopropanol (density 0.785 g/mL) was used as catalyst source. All experiments used the same molar ratio of catalyst as discussed above. All reactants and solvents were charged to the flask and heated to gentle reflux before the addition of catalyst. The starting time of the experiment was when the catalyst was added.

Reaction progress was monitored by removing a stopper from the fourth neck of the flask and sampling with a disposable pipet into a gas chromatograph autosampler vial. Gas chromatographic analysis, within a few seconds after sampling, provided an area percent of product which was used directly for all discussions in this specification unless otherwise noted.

The gas chromatographic analysis was conducted on a Hewlett Packard 5890 gas chromatograph equipped with a 15 meter×0.25 mm ID, Durabond-1 (0.25 micron thickness) column purchased from J & W Scientific Co. The gas chromatograph was operated on a program of 38° C. for 1 min followed by a temperature increase of 15° C./min until a temperature of 300° C. was reached at which point it was held for 5 minutes. A Hewlett Packard 3390 recording integrator was used for quantification.

Example 9

Figure 5:
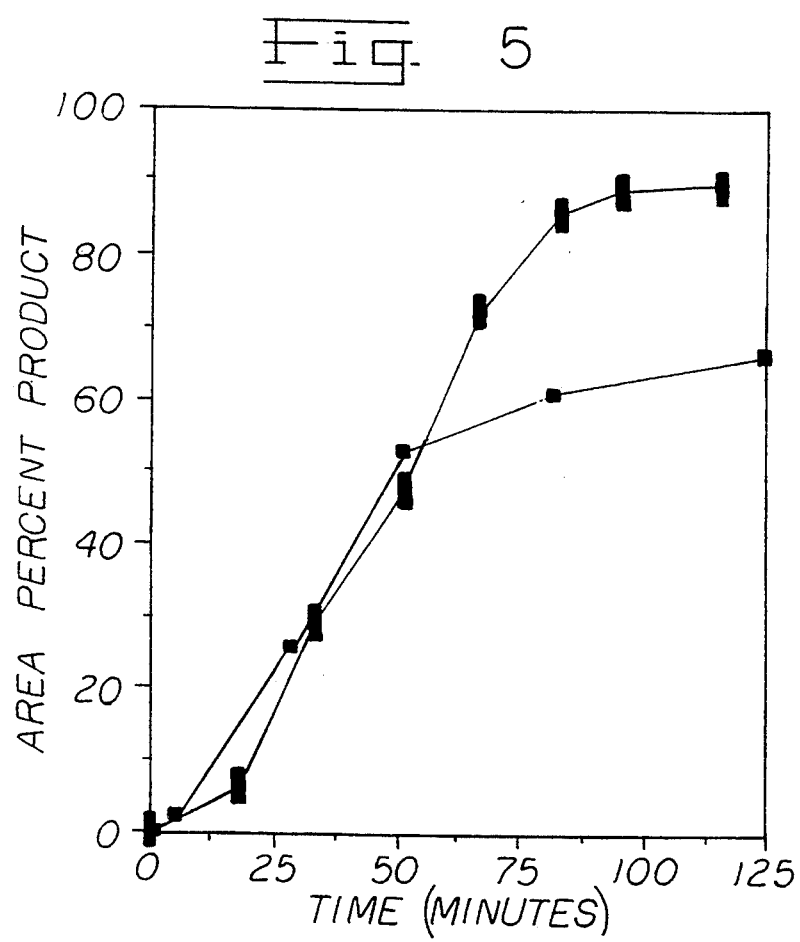
FIG. 5 plots the effect of diluent on reaction rates.

In this example the effect of diluent upon the reaction rate was checked by using hexane as solvent. The above procedure and apparatus was used along with 17.5 g $CH_3HSiCl_2$ (0.15 mole), 12.5 g cyclohexene (0.15 mole), 20 g hexane (0.23 mole) and 38 μL of chloroplatinic acid/IPA solution. Air was introduced subsurface at 9 mL/min. The reaction mixture was heated to 58° C. Comparison was made by running the experiment using 35 g $CH_3HSiCl_2$ (0.3 mole), 25 g cyclohexene (0.3 mole) and 76 μL of chloroplatinic acid/IPA solution. The effect of diluent upon reaction rate was small. The area percent of product shown in FIG. 5 wherein - - - ■ - - - ■ - - - ■ - - - is hexane diluent and - - - ■ - - - ■ - - - ■ - - -is no diluent, was corrected for the amount of hexane present.

Example 10

Figure 6:
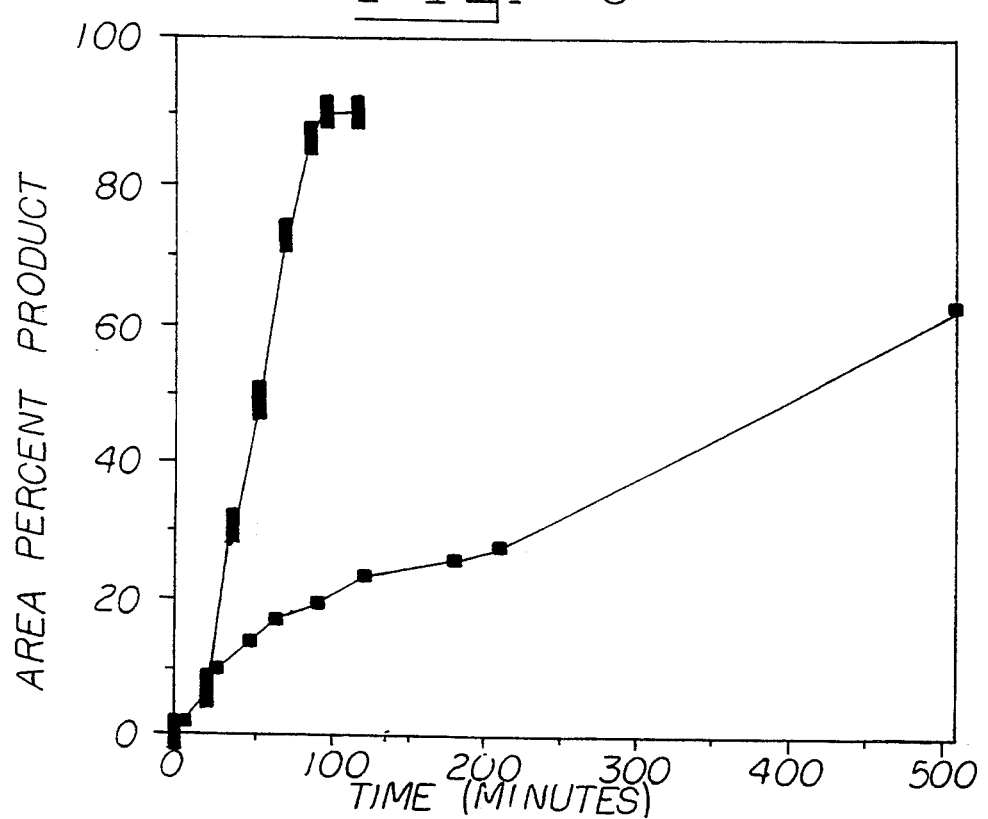
FIG. 6 shows the effects of varying the flow rate of air.

The importance of balancing the effects of deoxygenating by refluxing and oxygenating by air introduction is exemplified in this example where simply varying the flow rate of the oxygen source (air) drastically altered the rate of reaction. The above procedure and apparatus was used along with 35 g $CH_3HSiCl_2$ (0.3 mole), 25 g cyclohexene (0.3 mole) and 76 μL of chloroplatinic acid/IPA solution. Air was introduced subsurface at 200 mL/min. The reaction mixture was heated to 50° C. Comparison was made by running the experiment using 35 g $CH_3HSiCl_2$ (0.3 mole), 25 g cyclohexene (0.3 mole), and 76 µL of chloroplatinic acid/IPA solution and air added subsurface at 9 mL/min at 53° C. The effect of the rate of air addition is shown in FIG. 6 wherein --- ■ --- ■ --- ■ --- is air added at 200 mL/min and --- ▌ --- ▌ --- ▌ --- is air added at 9 mL/min. In the case of air introduced at 200 mL/min over-oxygenation occurred as discussed in Example 4 above.

Example 11

Figure 7:
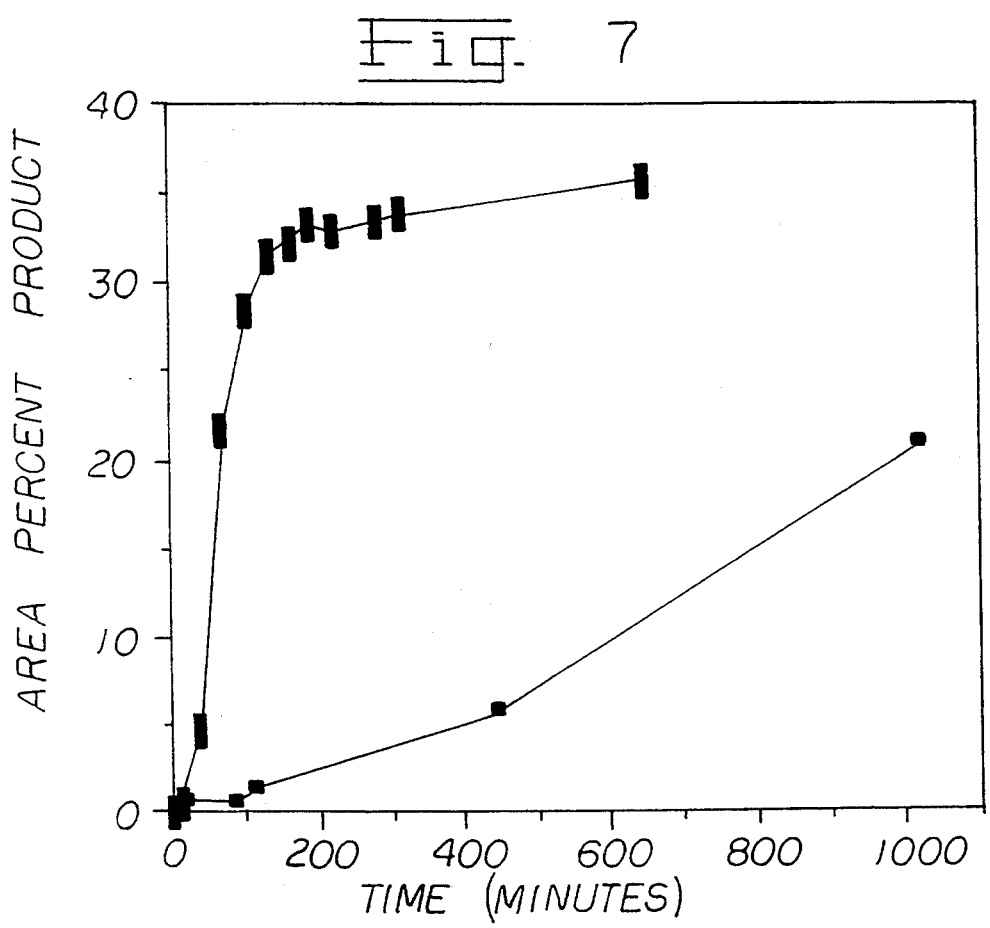
FIG. 7 shows the effect on reaction rate of controlling the amount of $O_2$ introduced in the reaction mixture.

The effect on reaction rate of controlling the amount of oxygen introduced into the reaction mixture is further exemplified by the hydrosilylation of cyclohexene by 1,1,1,2,3,3,3-heptamethyltrisiloxane. The above procedure and apparatus was used along with 33.8 g 1,1,1,2,3,3,3-heptamethyl-trisiloxane (0.15 mole), 12.5 g cyclohexene (0.15 mole), 20 g hexane, and 38 µL of chloroplatinic acid in isopropanol alcohol solution. Air or 2% Oxygen in nitrogen was introduced subsurface at 9 mL/min. The reaction mixture was heated to 82° C. The area percent products plotted in FIG. 7 wherein - --- ■ --- ■ --- ■ --- is air and --- ▌ --- ▌ --- ▌ --- is 2% oxygen in nitrogen, were not corrected for the amount of hexane present since it was identical in both cases. In the case of 2% oxygen, conversion to approximately 30 area percent product occurred, the reaction mixture was no longer deoxygenating itself sufficiently via reflux and the reaction rate slowed. In the case of air, the reaction rate was slow throughout due to the introduction of too much oxygen.

Example 12

The rate of the hydrosilylation of 1-hexene with methyldimethoxysilane is increased by oxygen enhancement. The above procedure and apparatus were used with $CH_3HSi(OCH_3)_2$ (15.93 g. 0.15 mol), 1-hexene (12.62 g. 0.15 mol) and hexane (20 g, 0.23 mol). The flask was purged with nitrogen at 9 mL/min. The solution was heated to reflux at 63° C. before addition of 38 µL of 10% by weight of $H_2PtCl_6 \cdot 6H_2O$ in IPA was injected into the boiling solution via a syringe. As soon as the chloroplatinic acid had been added, a sample was drawn for GC analysis which indicated that 0.5 area % of $CH_3(Hexyl)Si(OCH_3)_2$ formed. The reaction mixture was periodically analyzed by GC. After 24 hours under nitrogen, GC analysis showed less than 5 area % of hydrosilylated product was formed. At this time, air was introduced into the solution at 9 mL/min. After 16 hrs., GC analysis indicated that hydrosilylation went to completion and no $CH_3HSI(OCH_3)_2$ was left over.

Example 13

The rate of the hydrosilylation of 1-hexene with 1,1,1,2,3,3,3-heptamethyltrisiloxane is increased by oxygen enhancement. Hydrosilylation of 1-hexene was carried out using an equimolar ratio of 1-hexene/SiH in hexane at reflux. The solution was loaded into the flask and heated to reflux with nitrogen added subsurface before injecting the chloroplatinic acid/IPA catalyst solution. Samples were periodically drawn for GC analysis to follow the formation of the adduct. Several seconds after the catalyst was added, GC analysis showed the presence of only a trace amount of product. After three minutes, this amount had increased to 10% by area. It was found that in 14 minutes the clear solution had turned to dark brown color and the hydrosilylation reaction had gone to completion showing a 49.2 area % result. When the hydrosilylation of 1-hexene with 1,1,1,2,3,3,3-heptamethyltrisiloxane was performed under same conditions as above but under air, hydrosilylation to completion took place exothermically as soon as the chloroplatinic acid was injected into the solution of 1,1,1,2,3,3,3-heptamethyltrisiloxane/1-hexene/hexane at reflux. The clear color of the solution turned to dark brown color and the reaction was complete (51.9% by area) within seconds.

Example 14

Figure 8:
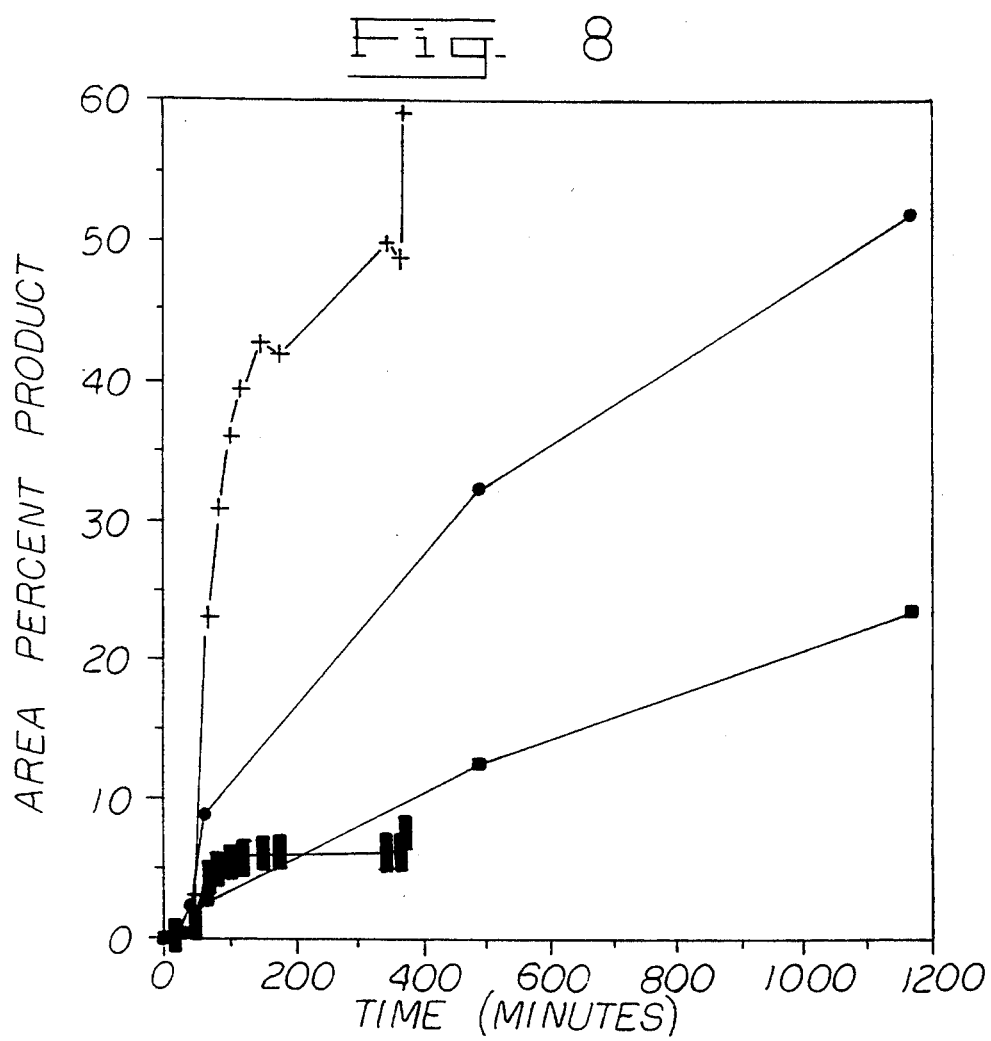
FIG. 8 shows the effect of various purges.

During the hydrosilylation of an internal olefin such as trans-2-hexene several adducts are possible. In addition to those possible by simple addition of the Si-H across the olefinic bond the products of migration of the olefinic double bond followed by addition of Si-H across the migrated bond are possible. Thus, in the case where one starts with an internal double bond, the predominate product is the same as if one had started with the terminal olefin. Such is the case with the following examples which use trans-2-hexene as starting material. The rate of the hydrosilylation of trans-2-hexene with 1,1,1,2,3,3,3-heptamethyltrisiloxane is increased by oxygen enhancement. It should be noted that the inventors herein have discovered that they can control the relative rates of double bond migration along the carbon backbone rather than the rate of hydrosilylation. Thus, the ratio of terminal adduct to internal adduct is affected by the use of oxygen enhancement. Hydrosilylation of trans-2-hexene was carried out using an equimolar ratio of hexene/SiH in hexane at reflux. It was found that when the hydrosilylation was conducted with a nitrogen purge, it went to completion in 21 hours while the same experiment with an air purge was complete in less than 6 hours. When the hydrosilylation was performed in the presence of the nitrogen purge, the hydrosilylated products were 69% terminal adduct with 31% internal adduct (mixture of 2-and 3-) but when hydrosilylation was performed in the presence of air, under the same conditions, the hydrosilylation formed 88% terminal adduct and 12% internal adduct all of which is illustrated in FIG. 8 wherein --- ■ --- ■ --- is nitrogen purge, internal adduct, --- ▌ --- ▌ ---is air purge, internal adduct, --- ● --- ● --- ● --- is nitrogen purge, terminal adduct and --- † --- † --- † - - -is air purge, terminal adduct.

EXAMPLE 15

The rate of the hydrosilylation of trans-2-hexene with triethylsilane is increased by oxygen enhancement. In experiments using 87 ppm Pt by weight to the total reactants and introducing either 2% oxygen in argon or pure argon, rate enhancements are exemplified in Table I. Reactants were in a 1:1 molar ratio and maintained at 65° C. throughout. The area percent product listed in Table I is a combination of isomers.

TABLE I

| Reaction of Trans-2-hexene with Triethylsilane | | |
|---|---|---|
| | Area Percent Product | |
| Atmosphere | 6 hrs. | 24 hrs. |
| Argon | 3.1 | 9.8 |
| 2% O$_2$/Argon | 4.7 | 16.0 |

EXAMPLE 16

The rate of hydrosilylation of trans-2-hexene by triethoxysilane is increased by oxygen enhancement. In experiments using 87 ppm Pt by weight to the total reactants and introducing either 2% oxygen in argon or pure argon, rate enhancements are exemplified in the table below. Reactants were in a 1:1 molar ratio and maintained at 65° C. throughout. The area percent product listed in Table II is a combination of isomers.

TABLE II

| Reaction of Trans-2-hexene with Triethoxysilane | | |
|---|---|---|
| | Area Percent Product | |
| Atmosphere | 7 hrs. | 24 hrs. |
| Argon | Trace | Trace |
| 2% O$_2$/Argon | 29.6 | 45.4 |

EXAMPLE 17

The rate of hydrosilylation of trans-2-hexene by phenyldimethylsilane is increased by oxygen enhancement. In experiments using 87 ppm Pt by weight to the total reactants and introducing either 2% oxygen in argon or pure argon, rate enhancements are exemplified in Table III. Reactants were in a 1:1 molar ratio and maintained at 65° C. throughout. The area percent product listed in Table III is a combination of isomers.

TABLE III

| Reaction of Trans-2-hexene with Phenyldimethylsilane | |
|---|---|
| Atmosphere | Area Percent Product @ 24 hrs. |
| Argon | 0.4 |
| 2% O$_2$/Argon | 6.4 |

EXAMPLE 18

The rate of the hydrosilylation of 1-hexene with triethylsilane is increased by oxygen enhancement. Hydrosilylation of 1-hexene was carried out using an equimolar ratio of 1-hexene/SiH in hexane at reflux. The solution was loaded into the flask and heated to reflux before injecting the chloroplatinic acid/IPA catalyst solution. Samples were periodically drawn for GC analysis to follow the formation of the adduct. When a nitrogen purge was used, hydrosilylation took place slowly with less than 12 area percent of adduct formed in 24 hr. But when an air purge was used, hydrosilylation went to near completion in 26 hr. forming 25 area % adduct. In addition, with air purge, 5 area percent of Et$_3$SiOSiEt$_3$ formed. No Et$_3$SiOSiEt$_3$ formed when the hydrosilylation was performed using nitrogen.

EXAMPLE 19

Figure 9:
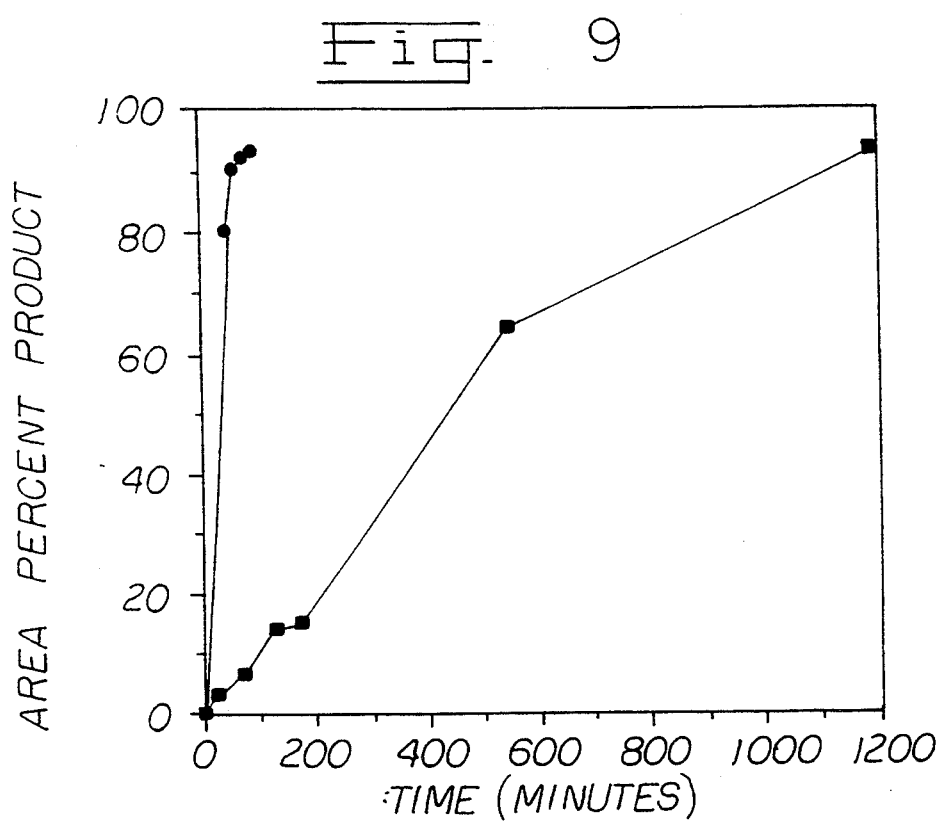
FIG. 9 shows the effects of high $O_2$ percentage containing gases.

The use of high percentage oxygen containing gases such as air to oxygenate certain silanes can be hazardous. The hazards can be avoided by the use of low percentage oxygen containing gases such as 2% oxygen in nitrogen. However, as pointed out in Example 2, hydrosilylation of cyclohexene by methyldichlorosilane, using 2% oxygen in nitrogen at atmospheric pressure drastically reduced the rate as compared to using air as an oxygen source. This can be compensated for by increasing temperature and optimizing 2% oxygen in nitrogen pressure to obtain the correct amount of oxygen in solution for maximum rate. The hydrosilylation rate at 53° C. and atmospheric pressure was compared to the rate at 110° C. and 80 psig. The rate data is shown in FIG. 9 wherein - - - ■ - - - ■ - - - is 2% O$_2$, 0 psig, and 53° C., and - - - ● - - - ● - - - is 2% O$_2$, 80 psig, and 110° C., respectively. The elevated temperature experiment was carried out in a stirred Parr reactor with subsurface addition of 2% oxygen in nitrogen at 1 cm$^3$/sec to 400 grams of 1:1 molar ratio mixture of cyclohexene and methyldichlorosilane containing 100 ppm chloroplatinic acid. It is obvious from the data that 2% oxygen in nitrogen pressure provided the correct concentration of oxygen in solution to give the optimum performance of the platinum catalyst.

EXAMPLE 20

The rate of hydrosilylation of 1,5-hexadiene by trichlorosilane was increased by oxygen enhancement. A 500 mL three-necked flask was equipped with a thermometer, magnetic stirrer bar, a pressure equalizing addition funnel connected to a gas source, a heating mantle and 19" water cooled condenser connected to a bubbler as a gas exit. To the flask was added 124 g of 1,5-hexadiene (1.51 mol) and 5 g of 1% platinum on carbon. No heat was applied to the flask until after the hydrosilylation had gone to completion as determined by GC analysis. The addition of 75.3 g of trichlorosilane (0.555 mol) to the 1,5-hexadiene was completed over a 60 minute period with stirring. During the addition the temperature increased to 50° C. when the hydrosilylation was carried out under air. GC analysis immediately after the addition was completed showed that the hydrosilylation had gone to completion as indicated by the complete absence of trichlorosilane. Excess 1,5-hexadiene was removed followed by the product, 5-hexenyltrichlorosilane having a boiling point of 56° C. at 2 to 3 Torr, 114.7 g, and 95% yield, by distillation.

The experiment was repeated exactly as described above with the exception that the addition of trichlorosilane to 1,5-hexadiene was conducted under nitrogen. During the trichlorosilane addition the temperature increased to 35° C. After the 60 minute addition period the reaction mixture was allowed to stir for an additional 150 minutes before a sample was withdrawn for GC analysis. GC analysis indicated the hydrosilylation had not gone to completion since 30% of the trichlorosilane remained unreacted. At this time the nitrogen head space purge was switched to air. Within two minutes after the system was switched to air the temperature rose to 50° C. GC analysis of the reaction mixture indicated the hydrosilylation had gone to completion as shown by the complete absence of trichlorosilane. Excess 1,5 hexadiene was removed followed by the product, 5-hexenyltrichlorosilane which had a boiling point of 56° C. at 2–3 Torr, 114.7 g, 95% yield, obtained by distillation.

EXAMPLE 21

Figure 10:
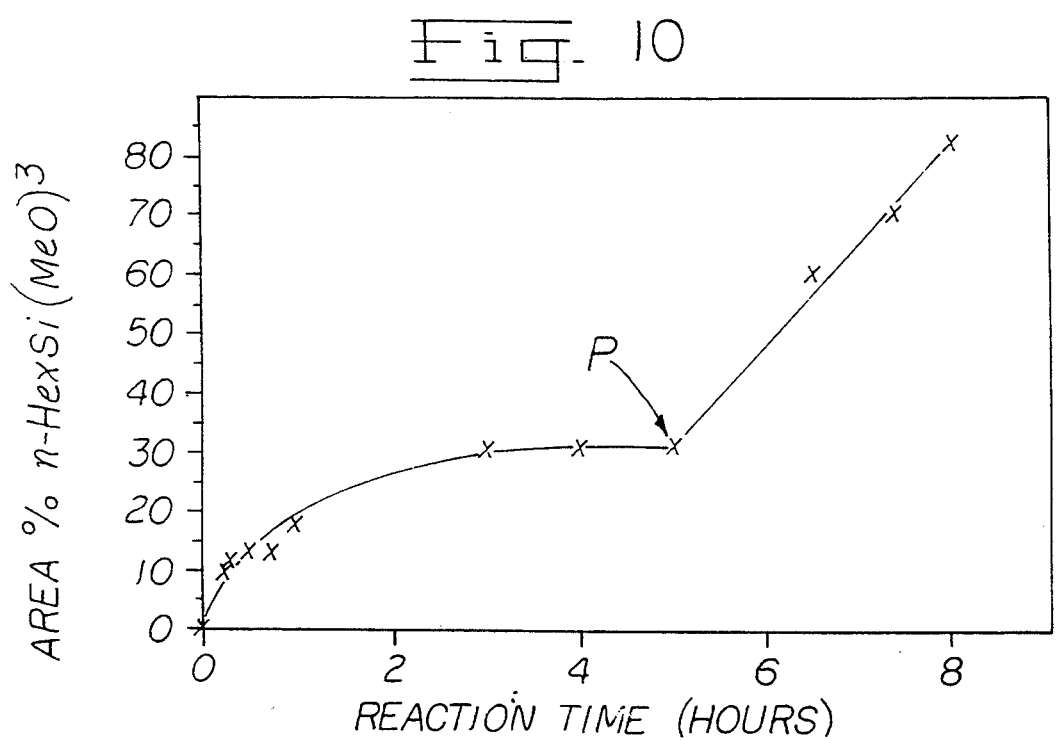
FIG. 10 plots reaction time.

The rate of hydrosilylation of 1-hexene by trimethoxysilane was increased by oxygen enhancement. A 50 mL three-necked flask was equipped with a septum, condenser, magnetic stirring bar and a heating mantle. The top of the condenser was fitted with a tee allowing the reaction mixture to be kept under the gas of choice. The flask was loaded with 12.2 g of trimethoxysilane (0.0998 mole), 8.39 g of 1-hexane (0.0998 mole) and 5.3 mg of chloroplatinic acid hexahydrate (1×10$^{-5}$ mol). The contents of the flask were heated to 50° C. under argon. Reaction progress was followed by GC analysis of aliquots withdrawn from the mixture. After 180 minutes the hydrosilylation had gone to 30% completion. After 300 minutes the hydrosilylation was still only 30% complete. The rate was restored by placing the flask under an air atmosphere. The rate data is shown in FIG. 10 wherein at point P, air was introduced to the reaction.

EXPERIMENTAL PROCEDURE
EXAMPLES 22–27

A. Sealed-tube Preparation

Pyrex glass tubes, with an approximate inner diameter of 4 mm and length of 11 inches, were sealed on one end and dried in air in a 140° C. oven overnight (at least 16 hours). The tubes were then removed from the oven, capped with a rubber septum, and allowed to cool to room temperature.

Three methods were used toward the preparation of samples in the sealed-tubes. Method 1 involved the addition of reaction mixture under laboratory atmosphere by uncapping a previously nitrogen-purged sealed-tube, adding the reaction mixture, then recapping the tube prior to flame-sealing. Method 2 involved the addition of reaction mixture under a nitrogen-inerted environment (glove bag) to a previously nitrogen-purged sealed-tube. Method 3 involved the addition of reaction mixture to a non-nitrogen-purged tube under laboratory atmosphere.

Approximately 0.8 ml of reaction mixture was added to each sealed-tube (unless noted) using a 1.0-ml syringe with needle. After addition of the reaction mixture, the sealed tubes were placed in a Dewar containing a dry ice/isopropanol mix, and flame-sealed using standard techniques.

B. Reactant Preparation

Cyclopentene was chilled in a dry ice/isopropanol mixture prior to the addition of dichlorosilane. All reaction components were mixed in ½-ounce vials inside a nitrogen-purged glove bag. Dichlorosilane was condensed in a modified Dewar condenser (filled with a dry ice/isopropanol mixture) equipped with an on-off valve which extended to the inside of the glove bag. This permitted the condensed dichlorosilane to be added to the chilled cyclopentene in an inerted environment.

C. Analysis

Reaction process was monitored using a Hewlett-Packard 5890A series gas chromatograph equipped with a thermal conductivity detector and a 3393A series integrator. The column (25 meter long by 0.02 mm ID) was a Hewlett-Packard Ultra 1 (crosslinked methyl silicone gum) capillary column which was operated at a helium head pressure of 52 psi. The column temperature was programmed from 35° C. to 270° C. at 15° C./minute with an initial holding time of 2 minutes at 35° C. A final holding time of 5 minutes was allowed at 270° C. The injection port and detector temperatures were 300° C. and 325° C., respectively. The split ratio was approximately 28:1. Sample injection volumes were approximately 0.8 μl.

Structural confirmation was accomplished using a Hewlett-Packard 5890A series gas chromatograph with flame detection and a 5971A series mass selective detector. The column (30 meters long by 0.25 mm ID) was a J & W Scientific (crosslinked methyl silicone gum—catalog no. 122-1032) capillary column which was operated at a helium head pressure of 18 psi. Sample injection volumes were approximately 0.1 μl.

D. Reagents

Reagents were used without further purification unless otherwise noted. Alumina used to treat some of the cyclopentene was conditioned at 150° C. for 71 hours over DRIERITE prior to use. The chloroplatinic acid solution represents a 10 wt % chloroplatinic acid in isopropanol. The Pt/C and Pt/Al$_2$O$_3$ were conditioned at 150° C. for 2 hours over DRIERITE prior to use.

EXAMPLE 22

Effect of Temperature

The following runs show the effect of temperature on the reaction between cyclopentene and dichlorosilane. The results of this Example may be found in Table 1. The results are given in calculated % yield based on GC area percent.

Run 1: Dichlorosilane (1.34 grams, 0.013 mole) was added to 8.50 grams (0.12 mole) of chilled cyclopentene. To this mixture, 10.6 μl of chloroplatinic acid catalyst solution was added. The reaction mixture (0.4 ml) was added to sealed-tubes using Method 1 and heated at 140° C. for 4, 8, and 24 hours.

Run 2: Dichlorosilane (2.40 grams, 0.024 mole) was added to 8.55 grams (0.13 mole) of chilled cyclopentene. To this mixture, 12.4 μl of chloroplatinic acid catalyst solution was added. The reaction mixture was added to sealed-tubes using Method 1 and heated at 170° C., 200° C., and 225° C., respectively for 4, 8, and 24 hours.

Run 3: Dichlorosilane (2.10 grams, 0.021 mole) was added to 8.50 grams (0.12 mole) of chilled cyclopentene. Chloroplatinic acid catalyst solution (10.6 μl) was added. The reaction mixture was added to sealed-tubes using Method 1 and heated at 250° C. for 4, 8, and 24 hours.

TABLE 1

| Run | Reaction Temperature | Reaction Time | Product* A | B | C |
|---|---|---|---|---|---|
| 1 | 140 | 4 | NA | NA | NA |
|   |   | 8 | 79.7 | 0 | 1.2 |
|   |   | 24 | 81.7 | 0.7 | 4.0 |
| 2 | 170 | 4 | 16.9 | 43.4 | 4.7 |
|   |   | 8 | 5.0 | 53.4 | 4.5 |
|   |   | 24 | 0.3 | 67.5 | 5.7 |
| 2 | 200 | 4 | 13.8 | 49.6 | 9.4 |
|   |   | 8 | 6.0 | 45.3 | 9.9 |
|   |   | 24 | 0.7 | 57.8 | 8.8 |
| 2 | 225 | 4 | 22.1 | 28.2 | 15.2 |
|   |   | 8 | 16.9 | 32.3 | 16.8 |
|   |   | 24 | 6.4 | 40.2 | 18.4 |
| 3 | 250 | 4 | 20.0 | 20.7 | 15.2 |
|   |   | 8 | 16.0 | 30.3 | 21.0 |
|   |   | 24 | 14.6 | 31.2 | 17.4 |

*A = Cyclopentyldichlorosilane, C$_5$H$_9$SiCl$_2$
B = Dicyclopentyldichlorosilane, (C$_5$H$_9$)$_2$SiCl$_2$
C = Cyclopentyltrichlorosilane, C$_5$H$_9$SiCl$_3$

Example 23

Effect of Catalyst Type

The following runs show the effect of the catalyst type on the reaction between cyclopentene and dichlorosilane. The results of this example may be found in Table 2.

Run 4: Dichlorosilane (2.01 grams, 0.020 mole) was added to 8.50 grams (0.12 mole) of chilled cyclopentene. To this mixture, 185 μl of a catalyst comprised of 3 wt % RhCl$_3$(n-Bu$_2$S)$_3$ in toluene was added. The reaction mixture was added to sealed-tubes using Method 1 and heated at 140° C. and 250° C., respectively, for 4, 8, and 24 hours.

Run 5: Dichlorosilane (1.77 grams, 0.018 mole) was added to 8.50 grams (0.12 mole) of chilled cyclopentene. This mixture was added to sealed-tubes using Method 1. A RhCl$_3$ catalyst (0.06 gram) was added to each sealed-tube. The reaction mixtures were heated at 140° C. and 250° C., respectively, for 4, 8, and 24 hours.

Run 6: Dichlorosilane (2.96 grams, 0.029 mole) was added to 8.52 grams (0.13 mole) of chilled cyclopentene. This mixture was added to sealed-tubes using Method 1. Pt/C catalyst (0.11 gram) was added to half of the sealed-tubes and Pt/Al$_2$O$_3$ catalyst (0.18 gram) was added to the remaining sealed-tubes. The reaction mixtures were heated at 170° C. for 4, 8, and 24 hours.

Run 7: Dichlorosilane (3.45 grams, 0.034 mole) was added to 8.50 grams (0.13 mole) of chilled cyclopentene. To this mixture, 90 μl of a catalyst comprised of 0.625 wt % of a divinyltetramethyldisiloxane platinum complex in a solution of dimethylvinyl terminated dimethyl siloxane was added. Sealed-tubes were prepared using Method 1 and heated at 170° C. for 4, 8, and 24 hours.

TABLE 2

| Run | Catalyst | Reaction Temp (°C.) | Reaction Time (hrs) | Product* A | B | C |
|---|---|---|---|---|---|---|
| 2 | H$_2$PtCl$_6$ | 170 | 4 | 16.9 | 43.4 | 4.7 |
|   |   |   | 8 | 5.0 | 53.4 | 4.5 |
|   |   |   | 24 | 0.3 | 67.5 | 5.7 |
| 4 | RhCl$_3$ (n-Bu$_2$S)$_3$ | 140 | 4 | 29.0 | 0.3 | 0.4 |
|   |   |   | 8 | 40.3 | 0.3 | 0.6 |
|   |   |   | 24 | 20.7 | 0.4 | 0.6 |
| 4 | RhCl$_3$ (n-Bu$_2$S)$_3$ | 250 | 4 | 25.6 | 5.9 | 12.6 |
|   |   |   | 8 | 22.2 | 8.9 | 17.2 |
|   |   |   | 24 | 9.8 | 16.1 | 21.9 |
| 5 | RhCl$_3$ | 140 | 4 | 0.6 | 0.7 | 16.8 |
|   |   |   | 8 | 0 | 0.6 | 14.4 |
|   |   |   | 24 | 0.2 | 0.6 | 12.3 |
| 5 | RhCl$_3$ | 250 | 4 | 0 | 0.4 | 12.3 |
|   |   |   | 8 | 0 | 0.5 | 14.5 |
|   |   |   | 24 | NA | NA | NA |
| 6 | Pt/C | 170 | 4 | NA | NA | NA |
|   |   |   | 8 | 16.2 | 4.7 | 5.4 |
|   |   |   | 24 | 8.5 | 6.1 | 3.6 |
| 6 | Pt/Al$_2$O$_3$ | 170 | 4 | 35.6 | 5.4 | 16.6 |
|   |   |   | 8 | 29.1 | 5.5 | 15.2 |
|   |   |   | 24 | 27.2 | 8.0 | 20.3 |
| 7 | Pt Complex | 170 | 4 | 81.3 | 1.5 | 1.4 |
|   |   |   | 8 | 76.4 | 2.1 | 1.3 |
|   |   |   | 24 | 65.8 | 11.6 | 3.5 |

*A = Cyclopentyldichlorosilane, C$_5$H$_9$SiCl$_2$
B = Dicyclopentyldichlorosilane, (C$_5$H$_9$)$_2$SiCl$_2$
C = Cyclopentyltrichlorosilane, C$_5$H$_9$SiCl$_3$ Example 24

Effect of Sealed-Tube Preparation

The following run shows the effect of the method by which the sealed tubes were prepared on the reaction between cyclopentene and dichlorosilane. The results of this example may be found in Table 3.

Run 8: Dichlorosilane (2.64 grams, 0.026 mole) was added to 8.56 grams (0.13 mole) of chilled cyclopentene. To this mixture, 12.8 μl of chloroplatinic acid catalyst solution was added. Sealed-tubes were prepared by Method 2 and by Method 3, and heated at 170° C. for 4, 8, and 24 hours.

TABLE 3

| Run | Tube Prep Method | Reaction Temp (°C.) | Reaction Time (hrs) | Product* A | B | C |
|---|---|---|---|---|---|---|
| 2 | 1 | 170 | 4 | 16.9 | 43.4 | 4.7 |
|   |   |   | 8 | 5.0 | 53.4 | 4.5 |
|   |   |   | 24 | 0.3 | 67.5 | 5.7 |
| 8 | 2 | 170 | 4 | 72.8 | 0.9 | 0.6 |
|   |   |   | 8 | 70.4 | 1.2 | 0.7 |
|   |   |   | 24 | 17.1 | 38.9 | 4.4 |
| 8 | 3 | 170 | 4 | 54.9 | 1.1 | 0.6 |
|   |   |   | 8 | 53.3 | 1.3 | 0.7 |
|   |   |   | 24 | NA | NA | NA |

*A = Cyclopentyldichlorosilane, C$_5$H$_9$SiCl$_2$
B = Dicyclopentyldichlorosilane, (C$_5$H$_9$)$_2$SiCl$_2$
C = Cyclopentyltrichlorosilane, C$_5$H$_9$SiCl$_3$ Example 25

Effect of Cyclopentene Supplier

The following runs show the effect of the source of the cyclopentene on the reaction between cyclopentene and dichlorosilane. The results of this example may be found in Table 4.

Run 9: Dichlorosilane (3.24 grams, 0.032 mole) was added to 8.50 grams (0.12 mole) of chilled cyclopentene (1). Similarly, 3.15 grams (0.031 mole) of dichlorosilane was added to 8.50 grams of chilled cyclopentene (2). In addition, 3.12 grams (0.031 mole) of dichlorosilane was added to 8.50 grams of chilled cyclopentene (3).

To each mixture, 13.0 μl of chloroplatinic acid catalyst solution was added. Sealed-tubes were prepared by Method 1 and heated at 170° C. for 4, 8, and 24 hours.

TABLE 4

| Run | Cyclo-pentene | Reaction Temp (°C.) | Reaction Time (hrs) | Product* A | B | C |
|---|---|---|---|---|---|---|
| 9 | 1 | 170 | 4 | 70.9 | 1.5 | 15.3 |
|   |   |   | 8 | 66.4 | 3.6 | 16.3 |
|   |   |   | 24 | 24.9 | 51.5 | 11.4 |
| 9 | 2 | 170 | 4 | 61.0 | 1.4 | 21.9 |
|   |   |   | 8 | 78.8 | 1.0 | 1.7 |
|   |   |   | 24 | 83.6 | 1.0 | 1.8 |
| 9 | 3 | 170 | 4 | 68.6 | 0.9 | 7.0 |
|   |   |   | 8 | 66.8 | 1.4 | 13.8 |
|   |   |   | 24 | 11.1 | 1.6 | 11.5 |

*A = Cyclopentyldichlorosilane, C$_5$H$_9$SiCl$_2$
B = Dicyclopentyldichlorosilane, (C$_5$H$_9$)$_2$SiCl$_2$
C = Cyclopentyltrichlorosilane, C$_5$H$_9$SiCl$_3$ Example 26

Effect of Alumina-Treated Cyclopentene

The following runs show the effect of treating the cyclopentene with alumina on the reaction between cyclopentene and dichlorosilane. The results of this example may be found in Table 5.

In the following runs the cyclopentene was treated by heating Al$_2$O$_3$ in an oven at 150° C. for several days. After several days the sample was removed from the oven in a closed container and placed in a N$_2$ glove bag. 8 inch drying tubes were filled with approximately 22 grams of the Al$_2$O$_3$. The cyclopentene was then poured through the tubes and collected into sample bottles.

Run 10: Dichlorosilane (4.02 grams, 0.040 mole) was added to 8.51 grams (0.12 mole) of chilled alumina-treated cyclopentene (2). Similarly, 3.72 grams (0.037 mole) of dichlorosilane was added to 8.50 grams (0.12 mole) of chilled untreated cyclopentene (2). To each mixture, 13.0 μl of chloroplatinic acid catalyst solution was added. Sealed-tubes were prepared by Method 1 and heated at 170° C. for 4, 8, and 24 hours.

Run 11: Dichlorosilane (3.22 grams, 0.032 mole) was added to 8.50 grams (0.13 mole) of chilled alumina-treated cyclopentene (1). To this mixture, 13.0 μl of chloroplatinic acid catalyst solution was added. Similarly, 0.71 grams (0.0070 mole) of dichlorosilane was added to 8.50 grams (0.13 mole) of chilled untreated cyclopentene (1). Chloroplatinic acid catalyst solution (4.2 μl) was added. Sealed-tubes were prepared according to Method 1 and heated at 170° C. for 4, 8, and 24 hours.

TABLE 5

| Run | Cyclo-pentene | Reaction Temp (°C.) | Reaction Time (hrs) | Product* A | B | C |
|---|---|---|---|---|---|---|
| 10 | Treated 2 | 170 | 4 | 91.0 | 1.1 | 0.5 |
|  |  |  | 8 | 82.2 | 8.7 | 2.1 |
|  |  |  | 24 | 38.2 | 49.6 | 5.4 |
| 10 | Untreated 2 | 170 | 4 | 77.5 | 0.6 | 0.8 |
|  |  |  | 8 | 81.0 | 0.8 | 0.9 |
|  |  |  | 24 | 80.3 | 1.5 | 1.6 |
| 11 | Treated 1 | 170 | 4 | 85.0 | 1.3 | 0.7 |
|  |  |  | 8 | 88.2 | 1.4 | 0.8 |
|  |  |  | 24 | 46.7 | 39.7 | 5.6 |
| 11 | Untreated 1 | 170 | 4 | 10.7 | 1.1 | 0.4 |
|  |  |  | 8 | 17.3 | 1.7 | 6.7 |
|  |  |  | 24 | 5.0 | 3.9 | 12.8 |

*A = Cyclopentyldichlorosilane, $C_5H_9SiCl_2$
B = Dicyclopentyldichlorosilane, $(C_5H_9)_2SiCl_2$
C = Cyclopentyltrichlorosilane, $C_5H_9SiCl_3$ Example 27

Reaction between cyclopentene and cyclopentyldichloro-silane. The results of this example may be found in Table 6.

Run 12: All reactants were chilled in a dry ice/isopropanol prior to mixing. Cyclopentyldichlorosilane (4.0 grams, 0.0024 mole of 98% pure) was added to 8.95 grams (0.131 mole) of cyclopentene in a ½-ounce vial. To this mixture, 12.3 μl of chloroplatinic acid catalyst solution was added. The catalyzed reaction mixture was added to nine sealed-tubes. An additional 12.3 μl of chloroplatinic acid catalyst solution was added to the final three tubes. The tubes were flame-sealed, and heated at 170° C. for 4, 8, and 24 hours.

TABLE 6

| Run | Reaction Temp (°C. | Reaction Time (hrs) | Product* A | B | C |
|---|---|---|---|---|---|
| 12 | 170 | 4 | 51.3 | 3.6 | 0.2 |
|  |  | 8 | 21.0 | 29.1 | 2.0 |
|  |  | 24 | 6.0 | 42.5 | 2.3 |
| 12 | 170 | 4 | 39.3 | 14.4 | 0.1 |
|  |  | 8 | 14.7 | 38.1 | 2.1 |
|  |  | 24 | 5.7 | 44.7 | 2.4 |
| 12 | 170 | 4 | 9.8 | 33.9 | 1.7 |
|  |  | 8 | 4.7 | 21.7 | 1.2 |
|  |  | 24 | 6.8 | 34.8 | 1.9 |

*A = Cyclopentyldichlorosilane, $C_5H_9SiCl_2$
B = Dicyclopentyldichlorosilane, $(C_5H_9)_2SiCl_2$
C = Cyclopentyltrichlorosilane, $(C_5H_9)_2SiHCl$

EXPERIMENTAL PROCEDURE

EXAMPLE 28

A. Reaction Equipment

The following runs were carried out in a 100-ml 3-neck round bottom flask was equipped with a thermometer and thermowatch, reflux condenser topped with a dry ice condenser which was connected to a bubbler, thermometer adaptor fitted with a 23 cm long disposable pipet for the subsurface addition of a gas which passed through a 10-inch long tube packed with DRI-ERITE ($CaSo_4$), heating mantle and magnetic stirring bar. Constant agitation was used throughout each Run.

B. Analysis

Analysis was performed as described in the SEALED-TUBE EXPERIMENTS.

C. Reagents

The reagents were the same and treated in the same manner as described in the SEALED-TUBE EXPERIMENTS unless otherwise specified. The cyclopentyldichlorosilane was produced in runs 13-17. The 2.07% oxygen (balance nitrogen) was purchased from AGA Specialty Gas, Maumee, Ohio. The air was lab air and by definition contains 78.08% nitrogen, 20.95% oxygen, 0.03% carbon dioxide, and 0.93% argon. The nitrogen was lab nitrogen.

Example 28

Reaction between cyclopentene and dichlorosilane.

The following are examples of the hydrosilylation of cyclopentene with cyclopentyldichlorosilane under various atmospheres to produce dicyclopentyldichlorosilane.

Run 13: Cyclopentene (10.24 grams), 16.95 grams of cyclopentyldichlorosilane (92.3% purity), and 15.85 grams of tridecane were added to the 100-ml round-bottom flask. To this mixture, 51.7 μl of chloroplatinic acid catalyst solution was added. An additional 44.11 grams of tridecane was added. Air was purged through the reaction mixture at 8 cc/min. for 3 hours. At this point a sample analysis showed a yield of 43.4% of cyclopentyldichlorosilane, 3.4% dicyclopentyldichlorosilane and 15.8% cyclopentyltrichlorosilane. Air was then purged through the reaction mixture at 16 cc/min. for an additional 4 hours. The temperature was allowed to vary from 135° C. to 140° C. At this point a sample analysis showed a yield of 2.7% of cyclopentyldichlorosilane, 8.4% dicyclopentyldichlorosilane and 46.5% cyclopentyltrichlorosilane. 2.07% oxygen in place of the air, was purged into the reaction mixture at 8 cc/minute for 3 hours. Temperature was held between 135° C. and 138° C. At this point a sample analysis showed a yield of 10.2% of cyclopentyldichlorosilane, 5.8% dicyclopentyldichlorosilane and 35.5% cyclopentyltrichlorosilane. After this time period, the 2.07% oxygen purge was increased to 16 cc/minute for 3 hours. Temperature was held between 135° C. and 137° C. At this point a sample analysis showed a yield of 6.5of cyclopentyldichlorosilane, 7.0% dicyclopentyldichlorosilane and 41.2% cyclopentyltrichlorosilane. The 2.07% oxygen purge was then increased to approximately 24 cc/minute for 1 hour 45 minutes. Temperature was held between 135° C. and 137° C. At this point a sample analysis showed a yield of 3.2% of cyclopentyldichlorosilane, 6.5% dicyclopentyldichlorosilane and 45.6% cyclopentyltrichlorosilane.

An additional 1.71 grams of cyclopentyldichlorosilane was added to the reaction mixture, and the 2.07% oxygen purge set to 16 cc/minute for 3 hours. Temperature was held between 155° C. and 160° C. At this point a sample analysis showed a yield of 8.5% of cyclopentyldichlorosilane, 6.8% dicyclopentyldichlorosilane and 45.3% cyclopentyltrichlorosilane.

Run 14: Cyclopentene (2.08 grams), 5.10 grams of cyclopentyldichlorosilane (81.5% purity), and 28.49 grams of tridecane was added to the 100-ml round-bottom flask. To this mixture 15.6 μl of chloroplatinic acid catalyst solution was added. Nitrogen was purged through the reaction mixture at 16 cc/minute for 10 hours. Temperature was allowed to vary between 150° C. and 173° C. At this point a sample analysis showed a yield of 52.9% of cyclopentyldichlorosilane, 0.5% dicyclopentyldichlorosilane and 1.8% cyclopentyltrichlorosilane. The reaction mixture was then subjected to an air purge at 16 cc/minute for 3 hours 10 minutes at a temperature ranging from 175° C. to 180° C. At this point a sample analysis showed a yield of 0.6% of cyclopentyldichlorosilane, 22.6% dicyclopentyldichlorosilane and 12.6% cyclopentyltrichlorosilane.

EXPERIMENTAL PROCEDURE
EXAMPLE 29-30

A. Reactant Preparation

Cyclopentene was chilled in a dry ice/isopropanol mixture prior to the addition of dichlorosilane. All reactants were mixed in a 1-gallon bottle inside a nitrogen-purged glove bag. Dichlorosilane was condensed in a modified condenser (filled with a dry ice/isopropanol mixture) equipped with an on-off valve which extended into the inside of the glove bag. This permitted the condensed dichlorosilane to be added to the chilled cyclopentene in an inert environment. This reaction mixture was transferred to a 1-gallon feed tank without exposure to laboratory atmosphere. The chloroplatinic catalyst solution was placed in the catalyst feed chamber (Runs 24–26). The catalyst was added directly to the reaction mixture in Runs 27 and 28. The reaction mixture and catalyst was fed into the He inerted 2-gallon reactor by pressuring the 1-gallon feed tank containing the reaction mixture.

B. Analysis

Reaction progress was monitored using a Hewlett-Packard 5890 series gas chromatograph equipped with a thermal conductivity detector. Data was collected, integrated, and reported using PC-based HP ChemStation software. The column was a 30 meter×0.25 mm ID×1.0 mm film OV-1 (Ohio Valley crosslinked and surface bonded dimethylpolysiloxane) capillary column which was operated at a helium head pressure of 10 psi. The column temperature was programed from 35° C. to 225° C. at 10° C./minute with an initial holding time of 5 minutes at 35° C. A final holding time of 5 minutes was allowed at 225° C. The injection port and detector temperatures were 250° C. and 275° C., respectively. Relevant instrument flows were: split vent flow =255 ml/min., septum purge flow=0.8 ml/min., column make-up flow=2.7 ml/min., detector reference gas flow=6.5 ml/min., and column flow=2.3 ml/min. Sample injection volumes were approximately 0.6 μl.

The results reported in Area % was converted to Weight % by the use of GLC response factors that were obtained by standard means.

Example 29

Step 1—Hydrosilylation of cyclopentene with dichlorosilane to produce cyclopentyldichlorosilane Dichlorosilane (657.4 grams-6.51 mole) was added to 2502 grams (36.73 mole) of chilled cyclopentene (2) in a one-gallon bottle. This reaction mixture was transferred to the 1-gallon feed tank. Chloroplatinic acid catalyst solution (3.3 ml) was added to the catalyst feed chamber. All reactants and catalyst were fed into an inerted, helium purged, 2-gallon reactor. The hydrosilylation was performed, with constant agitation, at a temperature ranging from 139.0° C. to 142.4° C. over an 8 hour period under a helium atmosphere. Reaction pressure ranged from 144 psig to 206 psig. At this point a sample analysis showed a yield of 82.8% of cyclopentyldichlorosilane, 11.5% cyclopentylchlorosilane, and 1.5% dicyclopentylchlorosilane.

Low boiling volatiles, particularly dichlorosilane, were stripped from the reaction mixture at atmospheric pressure and temperatures ranging from 45.4° C. to 48.2° C. (pot) and 38.0° C. to 41.7° C. (overhead) over a 1½ hour period, in ordinary lab glassware. At this point a sample analysis showed a yield of 88.5% of cyclopentyldichlorosilane, 9.8% cyclopentylchlorosilane, and 1.7% dicyclopentylchlorosilane.

Step 2—Hydrosilylation of cyclopentene with cyclopentyldichlorosilane to produce dicyclopentyldichlorosilane In the 2-gallon reactor, an additional 1467 grams of cyclopentene was added to the reaction mixture produced in Step 1 (stripped of chlorosilane). The mixture was agitated under a helium atmosphere at a temperature ranging from 170.0° C. to 177.0° C. for 2 hours. The pressure varied from 222 psig to 246 psig. At this point a sample analysis showed a yield of 91.0% of cyclopentyldichlorosilane, 6.7% cyclopentylchlorosilane, and 2.3% dicyclopentylchlorosilane.

The reaction mixture was subjected to a 2% oxygen purge with temperature ranging from 169.8° C. to 173.8° C. over a 3 hour period. The pressure was maintained between 300 psig to 314 psig over this period. The 2% oxygen accounted for 79 psig (on the average) above the vapor pressure of the reaction mixture. At this point a sample analysis showed a yield of 86.0% of cyclopentyldichlorosilane, 3.7% dicyclopentyldichlorosilane, 4.9% dicyclo-pentylchlorosilane and 5.4% cyclopentyltrichloro-silane.

The 2% oxygen was then reduced to a pressure which was maintained between 244 psig and 260 psig over a 4 hour period. Temperature remained between 170.1° C. and 171.8° C. over this period. The 2% oxygen accounted for 20 psig (on the average) above the vapor pressure of the reaction mixture. At this point a sample analysis showed a yield of 69.7% of cyclopentyldichlorosilane, 9.4% dicyclopentyldichlorosilane, 5.6% dicyclopentylchlorosilane and 15.3% cyclopentyltrichlorosilane.

The 2% oxygen was increased to a pressure which was maintained between 974 psig and 1040 psig over a 3 hour period. Temperature remained between 170.1° C. and 171.3° C. over this period. The 2% oxygen accounted for 776 psig (on the average) above the vapor pressure of the reaction mixture. At this point a sample analysis showed a yield of 49.7% of cyclopentyldichlorosilane, 12.8% dicyclopentyldichlorosilane, 5.7% dicyclopentylchlorosilane and 31.8% cyclopentyltrichlorosilane.

On another day, the reaction mixture was subjected to a helium atmosphere at a temperature ranging from 170.0° C. to 182.0° C. over 2 hours 15 minutes. Pressure was maintained between 216 psig and 258 psig throughout this period. At this point a sample analysis showed a yield of 44.0% of cyclopentyldichlorosilane, 15.9% dicyclopentyldichlorosilane, 5.8% dicyclopentylchlorosilane and 34.3% cyclopentyltrichorosilane.

The reaction mixture was then subjected to 0.57% oxygen (balance nitrogen) with temperature between 169.5° C. and 173.2° C. over 3 hours. Pressure was maintained between 262 psig and 276 psig over this period. The 0.57% oxygen accounted for 36 psig (on the average) above the vapor pressure of the reaction mixture. At this point a sample analysis showed a yield of 36.5% of cyclopentyldichlorosilane, 21.3% dicyclopentyldichlorosilane, 6.0% dicyclopentylchlorosilane and 36.2% cyclopentyltrichlorosilane. On the next day, an additional 1.5 mls. of chloroplatinic acid catalyst solution was added to the reaction mixture. The 0.57% oxygen was purged into the mixture at a temperature ranging between 169.7° C. and 171.1° C. over 5 hours 40 minutes.

Pressure was maintained between 256 psig and 274 psig throughout this period. The 0.57% oxygen accounted for 33 psig (on the average) above the vapor pressure of the reaction mixture. At this point a sample analysis showed a yield of 19.4% of cyclopentyldichlorosilane, 34.0% dicyclopentyldichlorosilane, 6.3% dicyclopentylchlorosilane and 40.3% cyclopentyltrichlorosilane.

Example 30

Step 1—Hydrosilylation of cyclopentene with dichlorosilane to produce cyclopentyldichlorosilane Dichlorosilane (654.3 grams-6.48 mole) was added to 2500.0 grams (36.70 mole) chilled cyclopentene (2). To this mixture, 3.3 ml of chloroplatinic acid catalyst solution was added. The reaction mixture and catalyst were transferred to the 1-gallon feed tank and, subsequently, fed into the inerted, helium purged, 2-gallon reactor. The hydrosilylation was performed, with constant agitation, at a temperature ranging from 138.6° C. to 143.5° C. for 9 hours under a helium atmosphere. At this point a sample analysis showed a yield of 86.6% of cyclopentyldichlorosilane, 9.3% cyclopentylchlorosilane, and 2.3% dicyclopentylchlorosilane. The reaction mixture was re-catalyzed by adding 3.3 mls of chloroplatinic acid catalyst solution after 5 hours 10 minutes of reaction. Reaction pressure ranged from 142 psig to 158 psig.

Low boiling volatiles, particularly dichlorosilane, were stripped from the reaction mixture at atmospheric pressure and temperatures ranging from 48.0° C. to 49.5° C. (pot) and 41.1° C. to 42.4° C. (vapor) over a 1-½ hour period, in common laboratory glassware. At this point a sample analysis showed a yield of 90.7% of cyclopentyldichlorosilane, 5.1% cyclopentylchlorosilane, 3.4% dicyclopentylchlorosilane and 0.8% cyclopentyltrichlorosilane.

Step 2—Hydrosilylation of cyclopentene with cyclopentyldichlorosilane to produce dicyclopentyldichlorosilane An additional 375.0 grams of cyclopentene (2) was added to the reaction mixture produced in Step 1 (stripped of dichlorosilane). The reaction mixture (in the 2-gallon reactor) was subjected to a 0.57% oxygen (balance nitrogen) purge with temperature ranging from 168.7° C. to 172° C. over a 6 hour period under a helium atmosphere. The pressure was maintained between 242 psig to 260 psig. The 0.57% oxygen accounted for 36 psig (on the average) above the vapor pressure of the reaction mixture. At this point a sample analysis showed a yield of 7.7% of cyclopentyldichlorosilane, 80.0% dicyclopentyldichlorosilane, 5.6% dicyclopentylchlorosilane and 6.7% cyclopentyltrichlorosilane.

What is claimed is:

1. A method of controlling hydrosilylation in a reaction mixture by controlling the solution concentration of oxygen relative to any platinum in said reaction mixture said hydrosilylation consisting essentially of: reacting
(A) a silicon hydride selected from silicon hydrides having the general formulae:

(i) $R_xSiH_{4-x}$
(ii) $R_yH_uSiX_{4-y-u}$
(iii) $R_z(R'O)_{4-z-w}SiH_w$

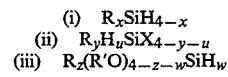

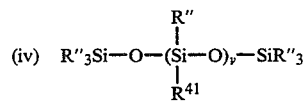

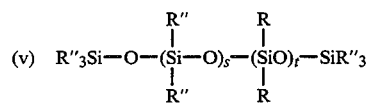

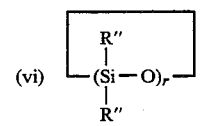

and

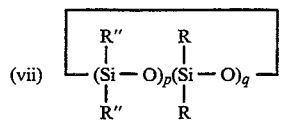

wherein each R is independently selected from the group consisting of substituted and unsubstituted alkyl groups of 1 to 30 carbon atoms and substituted, aryl groups of 6 to 16 carbon atoms; each R' is independently selected from alkyl groups of 1 to 6 carbon atoms; R" is independently selected from the group consisting of R and the hydrogen atom, with the proviso that at least one R" in each molecule is a hydrogen atom; p has a value of at least one; q has a value of at least 1 with the proviso that p+q has a value of 3 to 8; r has a value of 3 to 8; s has a value of 1 or greater; t has a value of 1 or greater; u has a value of 1, 2, or 3 with the proviso that u+y≦3; v has a value of zero or an integer of 1 or greater; w has a value of 1 to 3; x has the value of 1 to 3; y has a value of 0 to 2; and z has a value of 0 to 2 with the proviso that w+z≦3, with
(B) unsaturated compounds selected from the group consisting of
(i) substituted or unsubstituted unsaturated organic compounds or mixtures thereof, (ii) substituted or unsubstituted unsaturated silicon compounds or mixtures thereof and,
(iii) mixtures of (i) and (ii);
in the presence of a catalyst selected from the group consisting of
(a) platinum metal on a support,
(b) platinum compounds and,
(c) platinum complexes, wherein oxygen is added to the reaction mixture in controlled amounts during the course of the reaction whereby said hydrosilylation is controlled.

2. A method as claimed in claim 1 wherein the silicon hydride is a silane.

3. A method as claimed in claim 2 wherein the silane is $CH_3SiHCl_2$.

4. A method as claimed in claim 2 wherein the silane is $CH_3SiH(OCH_3)_2$.

5. A method as claimed in claim 2 wherein the silane is $(CH_3O)_3SiH$.

6. A method as claimed in claim 2 wherein the silane is $(CH_3CH_2O)_3SiH$.

7. A method as claimed in claim 2 wherein the silane is $(CH_3CH_2)_3SiH$.

8. A method as claimed in claim 2 wherein the silane is $(phenyl)(CH_3)_2SiH$.

9. A method as claimed in claim 2 wherein the silane is trichlorosilane.

10. A method as claimed in claim 2 wherein the silane is $(CH_3)_2HSiOCH_3$.

11. A method as claimed in claim 1 wherein the unsaturated compound is an organic unsaturated compound.

12. A method as claimed in claim 11 wherein the organic unsaturated compound is a cycloalkenyl compound.

13. A method as claimed in claim 12 wherein the cycloalkenyl compound is cyclohexene.

14. A method as claimed in claim 11 wherein the organic unsaturated compound is a linear alkenyl compound.

15. A method as claimed in claim 14 wherein the linear alkenyl compound is 1-hexene.

16. A method as claimed in claim 14 wherein the linear alkenyl compound is trans-2-hexene.

17. A method as claimed in claim 14 wherein the linear alkenyl compound is 1,5-hexadiene.

18. A method as claimed in claim 11 wherein the organic unsaturated compound is a branched alkenyl compound.

19. A method as claimed in claim 1 wherein the unsaturated compound is an organosilicon compound.

20. A method as claimed in claim 19 wherein the organosilicon compound is $CH_2=CHSi(OCH_3)_3$.

21. A method as claimed in claim 1 wherein the catalyst is a supported catalyst.

22. A method as claimed in claim 21 wherein the supported catalyst is platinum metal on carbon.

23. A method as claimed in claim 1 wherein the catalyst is a platinum compound.

24. A method as claimed in claim 23 wherein the platinum compound is chloroplatinic acid.

25. A method as claimed in claim 23 wherein the platinum compound is platinum chloride.

26. A method as claimed in claim 23 wherein the platinum compound is platinum oxide.

27. A method as claimed in claim 23 wherein the platinum compound is Karstedt's catalyst.

28. A method as claimed in claim 1 wherein the catalyst is a platinum complex.

29. A method as claimed in claim 28 wherein the platinum complex is dichlorobis(triphenylphosphine)platinum (II).

30. A method as claimed in claim 28 wherein the platinum complex is cis-dichlorobis(acetonitrile)platinum (II).

31. A method as claimed in claim 28 wherein the platinum complex is dicarbonyldichloroplatinum (II).

32. A method as claimed in claim 1 wherein any oxygen in solution is obtained by combining oxygen with an inert gas and introducing said combination to the reaction mixture at a controlled rate.

33. A method as claimed in claim 1 wherein any oxygen in solution is obtained by combining oxygen with an inert gas and introducing said combination to the reaction mixture at a controlled pressure.

34. A method as claimed in claim 1 wherein there is also present a solvent.

35. A method of controlling hydrosilylation in a reaction mixture by controlling the solution concentration of oxygen relative to any platinum in said reaction mixture said hydrosilylation consisting essentially of: reacting
(A) a silicon hydride having the general formula:

$$R_yH_uSiCl_{4-y-u}$$

wherein each R is independently selected from the group consisting of substituted and unsubstituted alkyl groups of 1 to 30 carbon atoms and substituted and unsubstituted aryl groups of 6 to 16 carbon atoms; u has a value of 1, 2, or 3 with the proviso that $u+y\leq 3$; y has a value of 0 to 2, with
(B) substituted or unsubstituted olefinically unsaturated alkenyl compounds selected from the group consisting of cycloalkenyl compounds having 4 to 8 carbon atoms, linear alkenyl compounds having 2 to 30 carbon atoms and branched alkenyl compounds having 4 to 30 carbon atoms, and mixtures thereof; in the presence of a catalyst selected from the group consisting of
(a) platinum metal on a support,
(b) platinum compounds and,
(c) platinum complexes,
wherein oxygen is added to the reaction mixture in controlled amounts during the course of the reaction whereby said hydrosilylation is controlled.

36. A method of controlling hydrosilylation in a reaction mixture by controlling the solution concentration of oxygen relative to any platinum in said reaction mixture said hydrosilylation consisting essentially of: reacting
(A) a silicon hydride having the general formula:

$$R_xSiH_{4-x}$$

wherein each R is independently selected from the group consisting of substituted and unsubstituted alkyl groups of 1 to 30 carbon atoms and substituted and unsubstituted aryl groups of 6 to 16 carbon atoms; x has a value of 1 to 3, with
(B) substituted or unsubstituted olefinically unsaturated alkenyl compounds selected from the group consisting of cycloalkenyl compounds having 4 to 8 carbon atoms, linear alkenyl compounds having 2 to 30 carbon atoms and branched alkenyl compounds having 4 to 30 carbon atoms, and mixtures thereof; in the presence of a catalyst selected from the group consisting of
(a) platinum metal on a support,
(b) platinum compounds and,
(c) platinum complexes,
wherein oxygen is added to the reaction mixture in controlled amounts during the course of the reaction whereby said hydrosilylation is controlled.

37. A method of controlling hydrosilylation in a reaction mixture by controlling the solution concentration of oxygen relative to any platinum in said reaction mixture said hydrosilylation consisting essentially of: reacting
(A) a silicon hydride having the general formula:

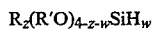

$$R_z(R'O)_{4-z-w}SiH_w$$

wherein each R is independently selected from the group consisting of substituted and unsubstituted alkyl groups of 1 to 30 carbon atoms and substituted and unsubstituted aryl groups of 6 to 16 carbon atoms; each R' is selected from alkyl groups having 1 to 6 carbon atoms; w has a value of 1 to 3, z has a value of 0 to 2, with the proviso that $z+w \leq 3$, with
(B) substituted or unsubstituted olefinically unsaturated alkenyl compounds selected from the group consisting of cycloalkenyl compounds having 4 to 8 carbon atoms, linear alkenyl compounds having 2 to 30 carbon atoms and branched alkenyl compounds having 4 to 30 carbon atoms, and mixtures thereof; in the presence of a catalyst selected from the group consisting of
(a) platinum metal on a support,
(b) platinum compounds and,
(c) platinum complexes,
wherein oxygen is added to the reaction mixture in controlled amounts during the course of the reaction whereby said hydrosilylation is controlled.

38. A method of controlling hydrosilylation in a reaction mixture by controlling the solution concentration of oxygen relative to any platinum in said reaction mixture said hydrosilylation consisting essentially of: reacting
(A) a silicon hydride having the general formula:

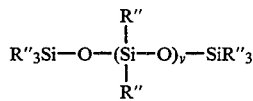

wherein each R" is independently selected from the group consisting of substituted and unsubstituted alkyl groups of 1 to 30 carbon atoms and substituted and unsubstituted aryl groups of 6 to 16 carbon atoms and hydrogen with the proviso that at least one R" be hydrogen; v has a value of zero or an integer of 1 or greater, with
(B) substituted or unsubstituted olefinically unsaturated alkenyl compounds selected from the group consisting of cycloalkenyl compounds having 4 to 8 carbon atoms, linear alkenyl compounds having 2 to 30 carbon atoms and branched alkenyl compounds having 4 to 30 carbon atoms, and mixtures thereof; in the presence of a catalyst selected from the group consisting of
(a) platinum metal on a support,
(b) platinum compounds and,
(c) platinum complexes,
wherein oxygen is added to the reaction mixture in controlled amounts during the course of the reaction whereby said hydrosilylation is controlled.

39. A method of controlling hydrosilylation in a reaction mixture by controlling the solution concentration of oxygen relative to any platinum in said reaction mixture said hydrosilylation consisting essentially of: reacting
(A) a silicon hydride having the general formula:

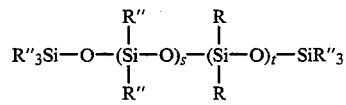

wherein each R is independently selected from the group consisting of substituted and unsubstituted alkyl groups of 1 to 30 carbon atoms and substituted, aryl groups of 6 to 16 carbon atoms; each R" is independently selected from the group consisting of substituted and unsubstituted alkyl groups of 1 to 30 carbon atoms and substituted and unsubstituted aryl groups of 6 to 16 carbon atoms and hydrogen with the proviso that at least one R" be hydrogen; s has a value of 1 or greater; and t has a value of 1 or greater; with
(B) substituted or unsubstituted olefinically unsaturated alkenyl compounds selected from the group consisting of cycloalkenyl compounds having 4 to 8 carbon atoms, linear alkenyl compounds having 2 to 30 carbon atoms and branched alkenyl compounds having 4 to 30 carbon atoms, and mixtures thereof; in the presence of a catalyst selected from the group consisting of
(a) platinum metal on a support,
(b) platinum compounds and,
(c) platinum complexes,
wherein oxygen is added to the reaction mixture in controlled amounts during the course of the reaction whereby said hydrosilylation is controlled.

40. A method of controlling hydrosilylation in a reaction mixture by controlling the solution concentration of oxygen relative to any platinum in said reaction mixture said hydrosilylation consisting essentially of: reacting
(A) a silicon hydride having the general formula:

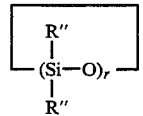

wherein each R" is independently selected from the group consisting of substituted and unsubstituted alkyl groups of 1 to 30 carbon atoms and substituted and unsubstituted aryl groups of 6 to 16 carbon atoms and hydrogen with the proviso that at least one R" be hydrogen; r has a value of 3 to 8; with
(B) substituted or unsubstituted olefinically unsaturated alkenyl compounds selected from the group consisting of cycloalkenyl compounds having 4 to 8 carbon atoms, linear alkenyl compounds having 2 to 30 carbon atoms and branched alkenyl compounds having 4 to 30 carbon atoms, and mixtures thereof; in the presence of a catalyst selected from the group consisting of
(a) platinum metal on a support,
(b) platinum compounds and,
(c) platinum complexes,
wherein oxygen is added to the reaction mixture in controlled amounts during the course of the reaction whereby said hydrosilylation is controlled.

41. A method of controlling hydrosilylation in a reaction mixture by controlling the solution concentration of oxygen relative to any platinum in said reaction mixture said hydrosilylation consisting essentially of: reacting
(A) a silicon hydride having the general formula:

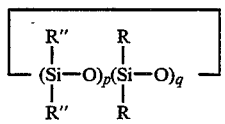

wherein each R is independently selected from the group consisting of substituted and unsubstituted alkyl groups of 1 to 30 carbon atoms and substituted, aryl groups of 6 to 16 carbon atoms; each R" is independently selected from the group consisting of substituted and unsubstituted alkyl groups of 1 to 30 carbon atoms and substituted and unsubstituted aryl groups of 6 to 16 carbon atoms and hydrogen with the proviso that at least one R" be hydrogen; p has a value of at least 1; q has a value of at least 1; with the proviso that p+q has a value of 3 to 8; with
(B) substituted or unsubstituted olefinically unsaturated alkenyl compounds selected from the group consisting of cycloalkenyl compounds having 4 to 8 carbon atoms, linear alkenyl compounds having 2 to 30 carbon atoms and branched alkenyl compounds having 4 to 30 carbon atoms, and mixtures thereof; in the presence of a catalyst selected from the group consisting of
(a) platinum metal on a support,
(b) platinum compounds and,
(c) platinum complexes,
wherein oxygen is added to the reaction mixture in controlled amounts during the course of the reaction whereby said hydrosilylation is controlled.

42. A method for producing dicycloalkylsubstituted silanes wherein the method comprises
(A) reacting
(I) a silane selected from the group consisting of
i) silanes having two hydrogen atoms attached to the silicon selected from the group consisting of $H_2SiX_2$ and $(R'O)_2SiH_2$ wherein each R' is independently selected from alkyl groups having 1 to 6 carbon atoms, and X is a halide;
ii) silanes having one hydrogen atom attached to silicon selected from the group consisting of $X_2R'''SiH$ and $R'''(R'O)_2SiH$ wherein each R' is independently selected from alkyl groups having 1 to 6 carbon atoms; and R''' is a cycloalkyl group having at least 4 carbon atoms, and X is a halide; and
iii) mixtures thereof; with
(II) an unsaturated cycloalkenyl compound containing at least 4 carbon atoms; in the presence of
(III) a hydrosilylation catalyst and
(IV) an effective amount of oxygen; and
(B) recovering the dicycloalkylsubstituted silane produced in (A).

43. A method as claimed in claim 42 wherein the silane is a silane having two hydrogen atoms attached to the silicon selected from the group consisting of $H_2SiX_2$ and $(R'O)_2SiH_2$ wherein each R' is independently selected from alkyl groups having 1 to 6 carbon atoms, and X is a halide.

44. A method as claimed in claim 43 wherein the silane is dichlorosilane.

45. A method as claimed in claim 42 wherein the silane is a silane having one hydrogen atom attached to silicon selected from the group consisting of $X_2R'''SiH$ and $R'''(R'O)_2SiH$ wherein each R' is independently selected from alkyl groups having 1 to 6 carbon atoms; and R''' is a cycloalkyl group having at least 4 carbon atoms, and X is a halide.

46. A method as claim in claim 45 wherein the silane is monocyclopentyldichlorosilane.

47. A method as claimed in claim 42 wherein the unsaturated cycloalkenyl compound is cyclopentene.

48. A method as claimed in claim 42 wherein the hydrosilylation catalyst is selected from the group consisting of rhodium compounds, platinum compounds, platinum metal on a support, platinum complexes and nickel compounds.

49. A method as claimed in claim 42 wherein the hydrosilylation catalyst is a platinum compound.

50. A method as claimed in claim 49 wherein the platinum compound is chloroplatinic acid.

51. A method as claimed in claim 42 wherein the oxygen is combined with an inert gas and introduced into the reaction mixture at a controlled rate.

52. A method as claimed in claim 51 wherein the oxygen is combined with nitrogen.

53. A method as claimed in claim 42 wherein the oxygen is combined with an inert gas and introduced into the reaction mixture at a controlled pressure.

54. A method as claimed in claim 42 wherein there is also present a solvent.

55. A method of controlling isomerization in linear or branched alkenyl compounds having at least 4 carbon atoms during a hydrosilylation reaction by introducing a controlled amount of oxygen into a reaction mixture during the hydrosilylation reaction wherein said hydrosilylation consists essentially of: reacting (A) a silicon hydride selected from silicon hydrides having the general formulae:

(i) $R_xSiH_{4-x}$
(ii) $R_yH_uSiX_{4-y-u}$
(iii) $R_z(R'O)_{4-z-w}SiH_w$

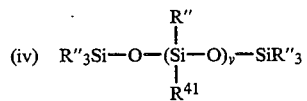

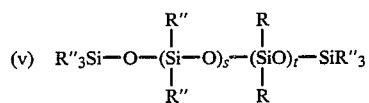

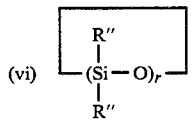

and

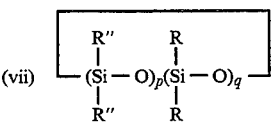

wherein each R is independently selected from the group consisting of substituted and unsubstituted alkyl groups of 1 to 30 carbon atoms and substituted, aryl groups of 6 to 16 carbon atoms; each R' is independently selected from alkyl groups of 1 to 6 carbon atoms; R" is independently selected from the group consisting of R and the hydrogen atom, with the proviso that at least one R" in each molecule is a hydrogen atom; p has a value of at least one; q has a value of at least 1 with the proviso that p+q has a value of 3 to 8; r has a value of 3 to 8; s has a value of 1 or greater; t has a value of 1 or greater; u has a value of 1, 2, or 3 with the proviso that u+y≦3; v has a value of zero or an integer of 1 or greater; w has a value of 1 to 3; x has the value of 1 to 3; y has a value of 0 to 2; and z has a value of 0 to 2 with the proviso that w+z≦3, with (B) a linear or branched alkenyl compound having at least 4 carbon atoms; in the presence of a catalyst selected from the group consisting of
(a) platinum metal on a support,
(b) platinum compounds and,
(c) platinum complexes,
wherein oxygen is added to the reaction mixture in controlled amounts during the course of the reaction whereby said isomerization is controlled.

* * * * *